(12) United States Patent  
Khandelwal et al.

(10) Patent No.: US 12,419,521 B2
(45) Date of Patent: Sep. 23, 2025

(54) SYSTEM TO DETECT FOOT ABNORMALITIES

(71) Applicant: Empo Health, Inc., San Bruno, CA (US)

(72) Inventors: Anuj Khandelwal, Palo Alto, CA (US); Eric Dahlseng, San Francisco, CA (US); Tyler Bond, San Francisco, CA (US)

(73) Assignee: Empo Health, Inc., San Bruno, CA (US)

( * ) Notice: Subject to any disclaimer, the term of this patent is extended or adjusted under 35 U.S.C. 154(b) by 0 days.

(21) Appl. No.: 18/616,095

(22) Filed: Mar. 25, 2024

(65) Prior Publication Data

US 2024/0260835 A1   Aug. 8, 2024

Related U.S. Application Data

(63) Continuation-in-part of application No. 18/172,207, filed on Feb. 21, 2023, now abandoned, which is a continuation of application No. PCT/US2021/046978, filed on Aug. 20, 2021.

(60) Provisional application No. 63/068,567, filed on Aug. 21, 2020.

(51) Int. Cl.
*A61B 5/00* (2006.01)

(52) U.S. Cl.
CPC .......... *A61B 5/0082* (2013.01); *A61B 5/0064* (2013.01); *A61B 5/702* (2013.01); *A61B 2562/0233* (2013.01)

(58) Field of Classification Search
None
See application file for complete search history.

(56) References Cited

U.S. PATENT DOCUMENTS

| | | | |
|---|---|---|---|
| 8,655,433 B2 | 2/2014 | Freeman et al. |
| 9,095,305 B2 | 8/2015 | Engler et al. |
| 9,212,814 B2 | 12/2015 | Puljan |
| 9,259,178 B2 | 2/2016 | Bloom et al. |
| 9,271,672 B2 | 3/2016 | Linders et al. |
| 9,301,688 B2 | 4/2016 | Goldish et al. |
| 9,326,723 B2 | 5/2016 | Petersen et al. |
| 9,737,263 B1 | 8/2017 | Kumar et al. |

(Continued)

FOREIGN PATENT DOCUMENTS

| | | |
|---|---|---|
| CN | 107307847 A | 11/2017 |
| CN | 108742519 A | 11/2018 |

(Continued)

OTHER PUBLICATIONS

Akkerman et al.; Large-area optical fingerprint sensors for next generation smartphones; SID:Society For Information Display; vol. 50; Issue 1; pp. 1000-1003; Jun. 2019.

(Continued)

*Primary Examiner* — Ashley K Buran
*Assistant Examiner* — Marjan Saboktakin
(74) *Attorney, Agent, or Firm* — Shay Glenn LLP

(57) ABSTRACT

Systems, devices, and methods for detecting a foot abnormality includes a platform configured to be stood upon by a user, an imaging device within the platform, and a processor connected to the imaging device. The processor is configured to detect a foot abnormality from images gathered by the imaging device.

20 Claims, 26 Drawing Sheets

(56) References Cited

U.S. PATENT DOCUMENTS

| | | | |
|---|---|---|---|
| 9,770,173 | B2 | 9/2017 | Panasyuk et al. |
| 9,901,298 | B2 | 2/2018 | O'Connor et al. |
| 9,955,900 | B2 | 5/2018 | O'Connor et al. |
| 10,028,676 | B2 | 7/2018 | Freeman et al. |
| 10,321,869 | B2 | 6/2019 | Freeman et al. |
| 10,635,885 | B2 | 4/2020 | Won et al. |
| 2005/0061332 | A1 | 3/2005 | Greenawalt et al. |
| 2005/0097762 | A1 | 5/2005 | Biesbrouck et al. |
| 2007/0211355 | A1 | 9/2007 | Dalbo et al. |
| 2013/0120804 | A1* | 5/2013 | Murray ............... H04N 1/1017 358/474 |
| 2013/0123587 | A1* | 5/2013 | Sarrafzadeh ......... A61B 5/7285 600/306 |
| 2013/0261494 | A1 | 10/2013 | Bloom et al. |
| 2014/0055590 | A1 | 2/2014 | Smith |
| 2014/0121479 | A1* | 5/2014 | O'Connor ............ A61B 5/447 600/407 |
| 2014/0275842 | A1 | 9/2014 | Curry et al. |
| 2015/0150457 | A1 | 6/2015 | Wu et al. |
| 2016/0015298 | A1* | 1/2016 | Danenberg .......... A61B 5/1079 600/476 |
| 2016/0256056 | A1 | 9/2016 | Petersen et al. |
| 2017/0319115 | A1 | 11/2017 | Cuccia et al. |
| 2017/0360298 | A1 | 12/2017 | Mougin et al. |
| 2019/0021649 | A1 | 1/2019 | Van Snellenberg et al. |
| 2019/0209076 | A1 | 7/2019 | Murphy et al. |
| 2019/0209093 | A1 | 7/2019 | Watts et al. |
| 2020/0107732 | A1 | 4/2020 | Cuccia et al. |
| 2020/0226891 | A1* | 7/2020 | Tran .................... H01Q 1/2291 |
| 2021/0004557 | A1 | 1/2021 | Tordera Salvador et al. |
| 2023/0200652 | A1 | 6/2023 | Kandelwal et al. |

FOREIGN PATENT DOCUMENTS

| | | |
|---|---|---|
| CN | 109414183 A | 3/2019 |
| DE | 202007011702 U1 | 2/2009 |
| DE | 102012101049 A1 | 8/2013 |
| JP | 2008078985 A * | 4/2008 |
| JP | 2018100853 A | 6/2018 |
| KR | 1881132 B1 | 7/2018 |
| WO | WO03/087717 A1 | 10/2003 |
| WO | WO2010/002840 A2 | 1/2010 |
| WO | WO2010/128519 A1 | 11/2010 |
| WO | WO2013/151705 A9 | 12/2014 |
| WO | WO2020/016569 A1 | 1/2020 |

OTHER PUBLICATIONS

Dhillon; Re-imagers; 4 pages; retrieved from the internet (http://www.vidhillon.staff.shef.ac.uk/teaching/phy217/instruments/phy217_inst_reimager.html); On May 25, 2023.

Han et al.; Image-based 3D object reconstruction: state-of-the-art and trends in the deep learning era; IEEE Transactions on Pattern Analysis and Machine Intelligence; 43(5); pp. 1578-1604; 27 pages; (Author Manuscript); Nov. 2019.

Jackson et al.; Large pose 3D face reconstruction from a single image via direct volumetric regression, IEEE International Conference on Computer Vision; pp. 1031-1039; 2017 (the year of publication is sufficiently earlier than the effective U. S. filing date and any foreign priority date so that the particular month of publication is not an issue ).

Pit'hova et al.; Differences in ulcer location in a diabetic foot syndrome; Vnitrni Lekaratvi; 53(12); pp. 1278-1285; Dec. 2007.

Wu et al.; Eulerian video magnification for revealing subtle changes in the world; 8 pages; retrieved from the internet (https://people.csail.mit.edu/mrub/papers/vidmag.pdf) on Apr. 2023.

* cited by examiner

SYSTEM TO DETECT FOOT ABNORMALITIES

CROSS REFERENCE TO RELATED APPLICATIONS

This application claims priority to U.S. application Ser. No. 18/172,207, filed on Feb. 21, 2023, which is a continuation of PCT Application No.: PCT/US2021/046978, filed on Aug. 20, 2021, which claims priority to Provisional Patent Application No. 63/068,567 filed Aug. 21, 2020, the entirety of which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Many types of foot complications, particularly when left untreated, can lead to serious issues in patients that progress through the various layers of tissue in the foot, even affecting bones. Foot complications that progress too far ultimately lead to amputations. Early intervention by medical professionals is often critical for ensuring that foot complications heal properly.

While foot complications can be caused by a number of different factors, they are often associated with diabetes and diabetic neuropathy. Patients with diabetic neuropathy usually have decreased sensation in their feet. This decreased sensation makes it difficult for these patients to feel foot complications as they develop, allowing foot complications to easily go unnoticed in the early stages.

Doctors typically examine the feet of at-risk patients for foot complications during routine visits. However, given the relatively low frequency of doctor visits compared with the rate of progression of many foot complications, doctors often rely on self-examinations by patients at home in order to catch foot complications as they develop. Unfortunately, many patients are unable to view all parts of their feet, don't understand what they are looking for, or simply forget to do their self-examinations.

Accordingly, a system or device to examine patients' feet for complications (outside of a doctor's office, such as in a patient's home) in a reliable and frequent way is desired so as to promote key medical interventions more quickly than relying on patient self-examinations alone.

SUMMARY OF THE DISCLOSURE

In general, in one embodiment, a device for detecting a foot abnormality (e.g., complication) includes a platform configured to be stood upon by a user, an imaging device within the platform, and a processor connected to the imaging device. The imaging device includes a large area imaging sensor configured to image a foot of a user standing on the platform. The processor is configured to detect a foot complication from images gathered by the imaging device.

In general, in one embodiment, a device for detecting a foot abnormality (e.g., complication) includes a bathmat configured to be stood upon by a user, an imaging device within the bathmat, and a processor connected to the imaging device. The imaging device is configured to image a foot of a user standing on the platform. The processor is configured to detect a foot abnormality (e.g., complication) from images gathered by the imaging device.

In general, in one embodiment, a system for detecting a foot abnormality includes a platform configured for engagement with a foot of a user, an imaging device within the platform having a large area imaging sensor configured to image the foot of the user while the foot is engaged with the platform, and a connector connected to the imaging device configured to communicate with a processor to detect a foot abnormality from a plurality of images gathered by the imaging device.

In general, in one embodiment, a system for detecting a foot abnormality includes a bathmat platform configured for engagement with a foot of a user, an imaging device within the bathmat platform configured to image the foot of the user while the foot is engaged with the bathmat platform, and a connector connected to the imaging device configured to communicate with a processor to detect a foot abnormality from a plurality of images gathered by the imaging device.

In general, in one embodiment, a system for detecting a foot abnormality includes a platform configured for engagement with a foot of a user, an imaging device within the platform, a sensor in or on the platform and configured to detect that the foot of the user has engaged with the platform, and a connector connected to the imaging device and the sensor, wherein the connector is configured to communicate with a processor to detect a foot abnormality from a plurality of images gathered by the imaging device. The imaging device is configured to automatically image the foot of the user after the sensor has detected that the foot of the user has engaged with the platform This and other embodiments can include one or more of the following features. The imaging device can include a large area imaging sensor configured to image the foot of the user while the foot is engaged with the platform. The system can further include the processor. The processor can be in the platform. The processor can be remote from the platform. The processor can be configured to issue an alert flag indicating suspicion of a foot abnormality based on the plurality of images gathered by the imaging device. The system can further include a plurality of side-facing cameras and/or wide-angle cameras on a vertical, raised side, or overhang of the platform. The system can further include a sensor in or on the platform and configured to detect that the user has stepped upon the platform. The imaging device can be configured to automatically image a foot of a user after the sensor has detected that the user has stepped upon the platform. A base of the platform can be less than 5 cm in height, less than 4 cm in height, or less than 3 cm in height. The platform can further include a scale configured to weigh the user. The system can further include a communication module configured to communicate with the user about a position of the user's foot on the platform and/or a stage of an imaging cycle. The imaging device can be configured to produce images of the foot within less than 10 seconds, within less than 5 seconds, within less than 3 seconds, or within less than 1 second of the sensor detecting that the user has stepped on the platform. The system can further include a collimator filter configured to achieve a tailored imaging depth. The large area imaging sensor can include a tailored imaging depth such that areas within 75 mm, within 50 mm, or within 40 mm are in focus and areas further away are not in focus. The processor can be configured to automatically detect an ulcer on the user's foot. The large area imaging sensor can include an array of photodetectors. The system can further include a sensor configured to detect a presence of the foot of the user. The imaging device can be configured to automatically begin imaging based upon a detection of the presence of the foot. The sensor can include a load sensor, pressure sensor, a capacitive proximity sensor, a heat sensor, or a light sensor. The system can further include a plurality of load sensors. The processor can be further configured to detect the foot abnormality based upon a force distribution of the foot detected by the plurality of load sensors. The processor can be wirelessly connected to the imaging device.

In general, in one embodiment, a system for detecting a foot abnormality includes a platform configured for engagement with a foot of a user, an imaging device within the platform configured to image the foot of the user when the foot is engaged with the platform so as to gather a plurality of images over time, and a processor connected to the imaging device. The processor can be configured to provide an indication of a changing condition of the foot over time based upon the plurality of images. The system can further include a large area imaging sensor configured to image the foot of the user while the foot is engaged with the platform. The processor can be in the platform. The processor can be remote from the platform. The processor can be configured to issue an alert flag indicating suspicion of a foot abnormality based on the plurality of images gathered by the imaging device. The system can further include a plurality of side-facing cameras and/or wide-angle cameras on a vertical, raised side, or overhang of the platform. The system can further include a sensor in or on the platform and configured to detect that the user has stepped upon the platform. The imaging device can be configured to automatically image a foot of a user after the sensor has detected that the user has stepped upon the platform. A base of the platform can be less than 5 cm in height, less than 4 cm in height, or less than 3 cm in height. The platform can further include a scale configured to weigh the user. The system can further include a communication module configured to communicate with the user about a position of the user's foot on the platform and/or a stage of an imaging cycle. The imaging device can be configured to produce images of the foot within less than 10 seconds, within less than 5 seconds, within less than 3 seconds, or within less than 1 second of the sensor detecting that the user has stepped on the platform. The system can further include a collimator filter configured to achieve an imaging depth. The large area imaging sensor can include a tailored imaging depth, such that areas within 75 mm, within 50 mm, or within 40 mm are in focus and areas further away are not in focus. The processor can be configured to automatically detect an ulcer on the user's foot. The large area imaging sensor can include an array of photodetectors. The system can further include a sensor configured to detect a presence of the foot of the user. The imaging device can be configured to automatically begin imaging based upon a detection of the presence of the foot. The one or more sensors can include a load sensor, pressure sensor, a capacitive proximity sensor, a heat sensor, or a light sensor. The system can further include a plurality of load sensors. The processor can be further configured to detect the foot abnormality based upon a force distribution of the foot detected by the plurality of load sensors. The processor can be wirelessly connected to the imaging device.

In general, in one embodiment, a method of detecting a foot abnormality includes automatically detecting that a foot of a user has engaged with an imaging platform, after the step of automatically detecting, imaging the foot of the user with an imaging device in the imaging platform to produce a plurality of images, and detecting a foot abnormality based upon the plurality of images.

In general, in one embodiment, a method of imaging a foot includes automatically detecting that a foot of a user has engaged with an imaging platform, after the step of automatically detecting, imaging a foot of the user with an imaging device in the imaging platform to produce at least one image, and automatically determining if a foot abnormality is present based upon the plurality of images.

This and other embodiments can include one or more of the following features. The step of automatically detecting can include automatically detecting before a user steps into or after a user steps out of a shower and/or while the user is standing or stepping in front of a sink. The step of imaging can include producing the plurality of images within 10 seconds of when the user has stepped onto the imaging platform. The imaging platform can be positioned in a bathroom. The method can further include notifying the user to reposition the user's foot or notifying the user of a status of an imaging cycle. The method can further include determining a weight of the user with the imaging platform. The method can further include sending an alert flag to a member of a care team at a remote location indicating that a foot abnormality was detected. The step of imaging can include imaging with a large area imaging sensor. The step of imaging can include imaging with a tailored imaging depth of within 75 mm, within 50 mm, or within 40 mm. Imaging can include imaging the plantar surface of the foot. The imaging platform can further include a plurality of wide-angle cameras, and imaging can further include generating a plurality of images of a side or tops of a toe or a side of a heel of the user. The method can further include generating a 3D visual model of the foot of the user based upon the plurality of images. The method can further include displaying an image of the foot abnormality on a remote display. The method can further include displaying a series of images taken over time of the foot of the user on a remote display. A first image of the series of images includes an image of the foot having the foot abnormality and a second image of the series of images includes an image of the foot not having the foot abnormality.

In general, in one embodiment, a device for detecting a foot abnormality includes a platform configured for engagement with a foot of a user, an imaging device within the platform configured to image the foot of the user when the foot is engaged with the platform, a processor connected to the imaging device. The processor is configured to detect a foot abnormality by gathering a plurality of images of a plantar surface and a lateral, medial, or dorsal surface of the foot with the imaging device, stitching the plurality of images together to form a three-dimensional model of the foot, and detecting an abnormality in the three-dimensional model indicative of a foot abnormality.

In general, in one embodiment, a device for detecting a foot abnormality includes a platform having a base configured for engagement with a foot of a user and an edge extending vertically upwards from the base, an imaging device within the base and the edge configured to image a plantar surface of a foot of the user from the base and to image a lateral, medial, or dorsal surface of the foot from the edge, and a processor connected to the imaging device configured to detect a foot abnormality from the captured images. In general, in one embodiment, a system for detecting a foot abnormality, including one or more or all of a platform, including a top layer with a first side and a second side, wherein the top layer comprises an optically clear tempered glass material, wherein the first side of the top layer is configured for engagement with a foot of a user; an imaging device within the platform, wherein the imaging device comprises a contact image sensor configured to image the foot of the user though the optically clear top layer while the foot is engaged with the top side of the platform, wherein the contact image sensor is configured to move relative to the top side of the platform to image the foot of the user; a pair of flexible spacers, each positioned against the second side of the top layer and at opposite ends of the contact image sensor, wherein the flexible spacers are configured to glide along the second side of the top layer, further wherein the flexible spacers are configured to deflect in response to a load on the top layer; a motor within the platform, wherein the motor is configured to drive the contact image sensor to move relative to the top side of the platform; a chassis within the platform and under the imaging device, wherein the chassis supports the imaging device, further wherein the chassis comprises a radiofrequency transparent material.

This and other systems can further include a processor.

In this and other systems, the processor is in the platform.

This and other systems, the processor is configured to issue an alert flag indicating suspicion of a foot abnormality based on the plurality of images gathered by the imaging device.

This and other systems, a base of the platform is less than 4 cm in height.

This and other systems, the platform further comprises a scale configured to weigh the user.

This and other systems can further include a plurality of load cells, wherein the load cells are positioned horizontally to the imaging device, relative to a plane of the top layer of the platform.

In this and other systems, the imaging device is configured to produce images of the foot within less than 4 seconds of the time the sensor detects that the user has stepped on the platform.

In general, in one embodiment, a system for detecting a foot abnormality, including one or more or all of: a platform, including a top layer with a first side and a second side, wherein the top layer comprises an optically clear tempered glass material, wherein the first side of the top layer is configured for engagement with a foot of a user; an imaging device within the platform, wherein the imaging device comprises a contact image sensor configured to image the foot of the user though the optically clear top layer while the foot is engaged with the top side of the platform, wherein the contact image sensor is configured to move relative to the top side of the platform to image the foot of the user; a motor within the platform, wherein the motor is configured to drive the contact image sensor to move relative to the top side of the platform;
  an encoder connected to the motor and configured to provide an output indicative of a contact image sensor position, wherein a controller is configured to use the output to direct the imaging device to obtain images when the contact image sensor is accelerating or decelerating; and
  a chassis within the platform and under the imaging device, wherein the chassis supports the imaging device, further wherein the chassis comprises a radiofrequency transparent material.

This and other systems can further include a processor.

In this and other systems, the processor is in the platform.

In this and other systems, the processor is configured to issue an alert flag indicating suspicion of a foot abnormality based on the plurality of images gathered by the imaging device.

The system of claim 1, wherein a base of the platform is less than 4 cm in height.

In this and other systems, the platform further comprises a scale configured to weigh the user.

This and other systems can further include a plurality of load cells, wherein the load cells are positioned horizontal to the imaging device, relative to a plane of the top layer of the platform.

In this and other systems, the imaging device is configured to produce images of the foot within less than 4 seconds of the time the sensor detects that the user has stepped on the platform.

In general, in one embodiment, a system for detecting a foot abnormality, including one or more or all of a platform, including a top layer with a first side and a second side, wherein the top layer comprises an optically clear tempered glass material, wherein the first side of the top layer is configured for engagement with a foot of a user; an imaging device within the platform, wherein the imaging device comprises a contact image sensor configured to image the foot of the user though the optically clear top layer while the foot is engaged with the top side of the platform, wherein the contact image sensor is configured to move relative to the top side of the platform to image the foot of the user; a pair of flexible spacers, each positioned against the second side of the top layer and at opposite ends of the contact image sensor, wherein the flexible spacers are configured to glide along the second side of the top layer, further wherein the flexible spacers are configured to deflect in response to a load on the top layer; a motor within the platform, wherein the motor is configured to drive the contact image sensor to move relative to the top side of the platform; an encoder connected to the motor and configured to provide an output indicative of a contact image sensor position, wherein a controller is configured to use the output to direct the imaging device to obtain images when the contact image sensor is accelerating or decelerating; and a chassis within the platform and under the imaging device, wherein the chassis supports the imaging device, further wherein the chassis comprises a radiofrequency transparent material.

A method of imaging a foot, including one or more or all of the steps of automatically detecting that a foot of a user has engaged with an imaging platform; deflecting, with a load from the foot of the user, a top layer of the imaging platform; flexing a pair of flexible spacers, wherein each flexible spacer is positioned against the second side of the top layer and at opposite ends of an imaging device, wherein the flexible spacers are configured to glide along the second side of the top layer during device imaging; driving, with a motor, an imaging device in the imaging platform to move relative to the foot of the user, wherein the imaging device comprises a contact image sensor; obtaining, with an encoder connected to the motor, an output indicative of a contact image sensor position, when the imaging device is accelerating or decelerating; directing, with a controller, the imaging device to produce a plurality of images when the imaging device is accelerating or decelerating; and processing the plurality of images to obtain a foot image.

These and other methods can further include a step of detecting a foot abnormality based upon the plurality of images.

These and other methods can further include a step of automatically determining if a foot abnormality is present based upon the plurality of images.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 17A shows a large area imaging sensor with an array of photodetectors and a lighting element below the array. FIG. 17B shows a large area imaging sensor with an array of photodetectors with a lighting element above the array. FIG. 17C shows a large area imaging sensor with an array of photodetectors with a lighting element within the array.

FIG. 19A shows a schematic of a plantar image of a patient's foot with a foot ulcer. FIG. 19B shows a schematic of a side image of the patient's foot. The side image in FIG. 19B can incorporate data from the image taken in FIG. 19A.

FIG. 25A illustrates the side-facing cameras in a vertical or raised side of the platform. FIG. 25B illustrates the overlapping angle of views of the side-facing cameras for generating stereo images and a 3D model of a user's feet.

DETAILED DESCRIPTION

Described herein are systems, devices, and methods for detecting early-stage foot abnormalities (also referred to herein as foot complications or complications (e.g., complications caused by repetitive stress/pressure, trauma, vascular irregularities, and/or infections, such as an ulcer, callus, fungus, deformed toenail, wound, and/or laceration) to any part of the leg or foot (e.g., the plantar, lateral, medial, or dorsal parts of the foot, toes, toenails, heel, and/or ankle).

The system can use images, including images generated within the visual spectrum of light and images generated within a spectrum of light outside of the visual range (e.g., within the infrared spectrum), to identify foot complications. In some embodiments, the system can include a platform that includes a flat mat configured to image the plantar surface of the feet and/or additional element(s) configured to image the lateral, medial, and dorsal parts of feet. In some embodiments, plantar pressure or force distributions and/or temperature/infrared readings can be used in combination with the generated images to detect complications. In some embodiments, the system can be connected via a network for detection of complications and/or can trigger a notification when complications are identified.

Figure 1:
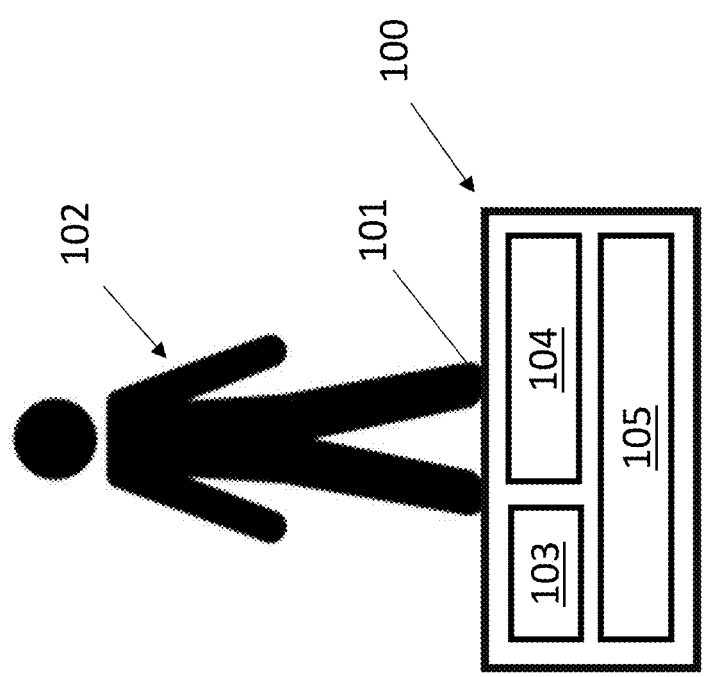
FIG. 1 is a schematic showing use of an exemplary foot complication detection system.

Referring to FIG. 1, an exemplary foot complication system is shown. FIG. 1 shows a detection platform 100 (e.g., a mat or raised surface) configured to screen the bottom of a patient's foot 101 when the patient 102 steps barefoot onto the platform 100 for early indicators and risk factors for foot complications. The platform 100 can include one or more presence sensors 103 to detect the presence of the patient 102 and an imaging device 104 to take an image of the foot 101. In some embodiments, the presence sensors can be one or more load or pressure sensors to detect when a force or pressure is applied (e.g., by the foot) on the platform 100. In some embodiments, the presence sensors 103 can be one or more ambient light sensors to detect when a light in the room (e.g., bathroom) is turned on and/or a shadow is cast over the platform 100. In other embodiments, the presence sensors 103 can be one or more capacitive or other proximity sensors to detect when a patient is close to the platform 100.

The imaging device 104 can be configured to take images of the foot 101 (e.g., of the plantar, anterior, posterior, lateral, medial, and/or dorsal surfaces). The platform 100 can further include a platform processor 105 configured to analyze the images taken with the imaging device 104 to detect foot complications. The one or more presence sensors 103 can be used to detect when a person steps on the platform 100. In some embodiments, this detection can be used to trigger the imaging device 104 and/or platform processor 105. The platform 100 can further include a battery and/or power cord and/or can be configured for wireless charging.

The platform 100 can be used, for example, as a bathmat. To function as a bathmat, for example, the platform 100 can be waterproof and/or water wicking, can include texturing, can include an active drying mechanism, can have a pattern thereon with multiple materials to absorb, or can include light-transmissive sections or light guides within a water-absorptive material. Further, the platform 100 (or the base of the platform, excluding a vertical or raised side, overhang, etc.) can be 5 cm or less in height, such as 4 cm or less in height, 3 cm or less in height, or 2 cm or less in height Referring to FIG. 2, in some embodiments, the platform 100 (which can be, for example, in a bathroom next to a sink 221) can be connected to a remote processor 222 (for example, via a connector such as an Ethernet cable connection, wireless internet card, direct internet connection, a cellular connector, Wi-Fi, or Bluetooth). The remote processor 222 can be used in lieu of or in addition to the platform processor 105 in the platform 100 or any other platform described herein. In some embodiments, the platform 100 can be connected to a local or platform processor 105 via a connector, such as a data cable. In some embodiments, for example, the platform processor 105 can combine data from multiple sensors 103 together into one packet (e.g., images from multiple image sensors and/or data from presence sensors), adding additional size and position information based on which sensor(s) 103 the data comes from, while the remote processor 222 can create the visual model and perform the analysis to detect foot complications. In some variations, a system for detecting a foot complication may have multiple processors, such as one or more than one remote processor and one or more than one platform processor. In some variations, platform processor 105 and remote processor 222 may be configured to perform the same or similar functions (e.g., platform processor 105 and remote processor 222 may be redundant and be configured to perform redundant functions). A user may choose which type of processor(s) to use with a system. As used herein, unless otherwise indicated, processor may refer to a remote processor and/or a platform processor.

Figure 22:
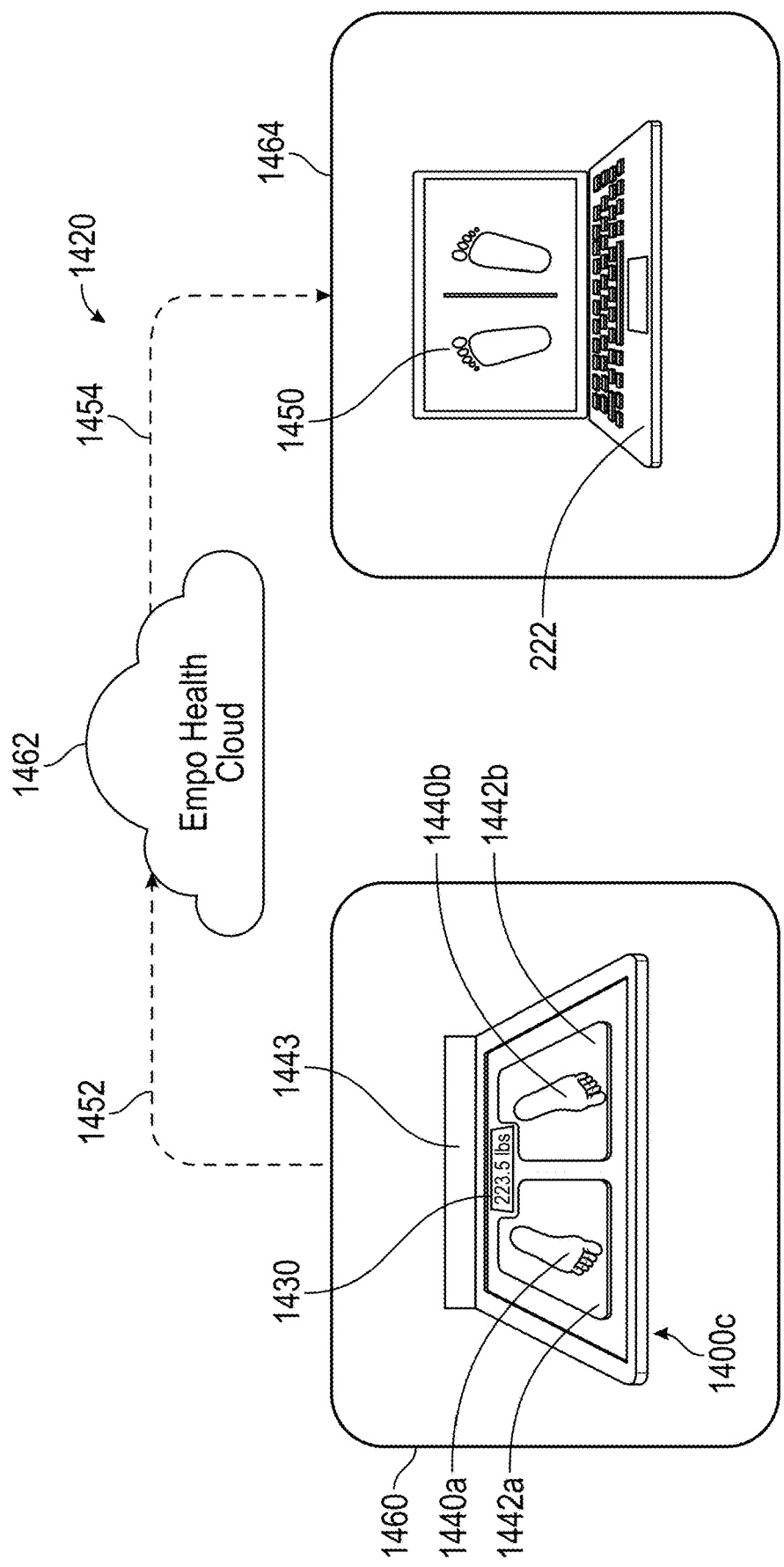
FIG. 22 is a schematic illustration of an automatic foot complication detection system with remote image processing.

Referring to FIG. 22, system 1420 for detecting a foot complication is configured to issue an alert and/or communicate an alert flag to a patient or a member of a care team at a remote location. The alert flag can be issued and/or communicated to indicate data generation and/or detection of a foot abnormality (e.g., a foot complication). As illustrated in FIG. 22, platform 1400c can take one or more images of a patient's foot (not shown) and/or generate other data at site of use 1460. The platform 1400c can then, via one or more connectors such as a data cable, an Ethernet cable connector or a wireless card, send the one or more images to a processor, send (arrow 1452) the one or more images of the patient's foot and other data taken at platform 1400c at site of use 1460 to internet cloud 1462 (e.g., a first remote processor). Cloud 1462 can store and/or analyze the images and associated data and send (arrow 1454) an alert flag to remote location 1464, such as to remote processor 222 (a second remote processor in this example) or to another remote receiver. Remote processor 222 or another remote receiver may be monitored by a member of a care team, such as a doctor, a nurse, other caregiver, or a family member. Remote processor 222 may generate visual model 1450 showing a visual model of the patient's foot, and a member of the care team may view the visual model 1450. The visual model 1450 may be especially useful for a member of the care team to help determine the nature of a foot complication or foot concern and next steps (if any are needed) to help the patient. In some variations, platform processor 105 or cloud 1462 may 1462 may generate a visual model, and remote processor 222 may receive the generated visual model, e.g., from platform processor 105 or cloud 1462. In some examples, the alert flag may be sent to remote processor 222 only if a foot complication, foot abnormality, or other concern is detected by system 1420. In some variations, the alert flag can be sent even if a foot complication, foot abnormality, or other concern is not detected, such as whenever an analysis is performed or on a regular basis. In some variations, when image analysis and/or data analysis are performed locally by platform processor 105, platform processor 105 can send an alert flag to cloud 1462 (which can send an alert flag to remote processor 222) or can send an alert flag directly to remote processor 222 (such as if a system for detecting a foot complication is not connected to a cloud). The remote processor can be, for example a computer, a monitor, or a smart phone. The remote processor can be monitored by a member of a care team, such as a doctor, a nurse, or a family member. The alert flag can be, for example, an audible alert (e.g., an alarm, a beep, a phone call, a voicemail) and/or a visual alert (e.g., an email, a colored light, a message, a pop-up, a text.)

Further, the platform processor 105 or remote processor 222 can be configured to send and/or make available raw data, processed or analyzed data, and/or notifications to patients and/or their providers and/or other members of their care team, for example their family. In some embodiments, for example, gathered and/or analyzed data can be accessed through a web browser or application-based service. In some embodiments, the user and/or provider can receive notifications on an app or via text message. In some embodiments, the user and/or provider can receive notifications via a communications module (a local (platform) communication module or a remote communication module), such as a speaker or lights on the platform 100 and/or on the remote processor 222 or other remote receiver. In some embodiments, the notifications can include alerts to the user to reposition the feet for better reading and/or where to reposition the feet to, alerts to indicate the timing in an imaging cycle (e.g., whether the user can move his or her feet/leave the platform), alerts to see a doctor, and/or alerts that a complication has or has not been detected.

Figure 21A:
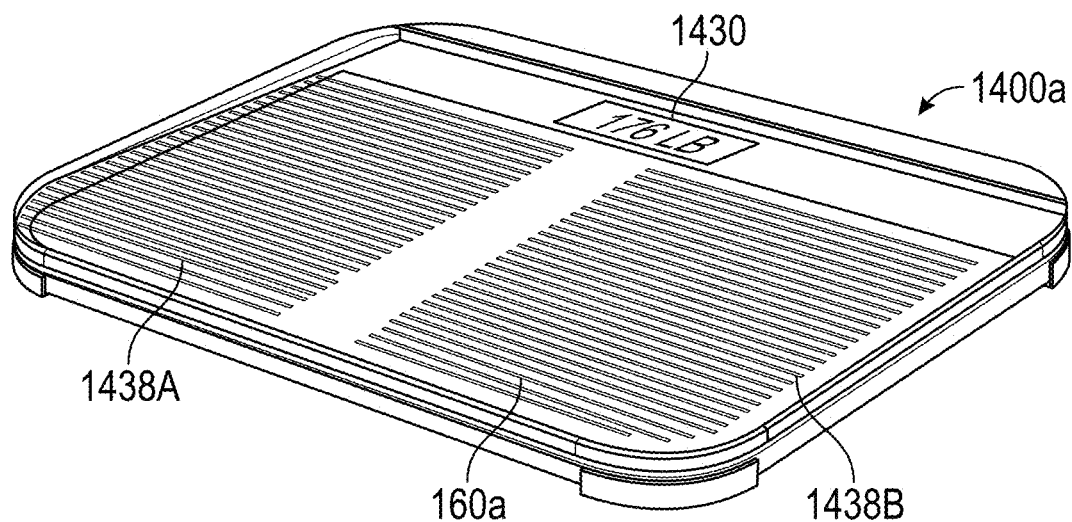
FIG. 21A shows a schematic of a platform of a foot complication detection system configured to perform multiple functions, including a scale for measuring a patient's weight as well as a foot and leg imager.
Figure 21B:
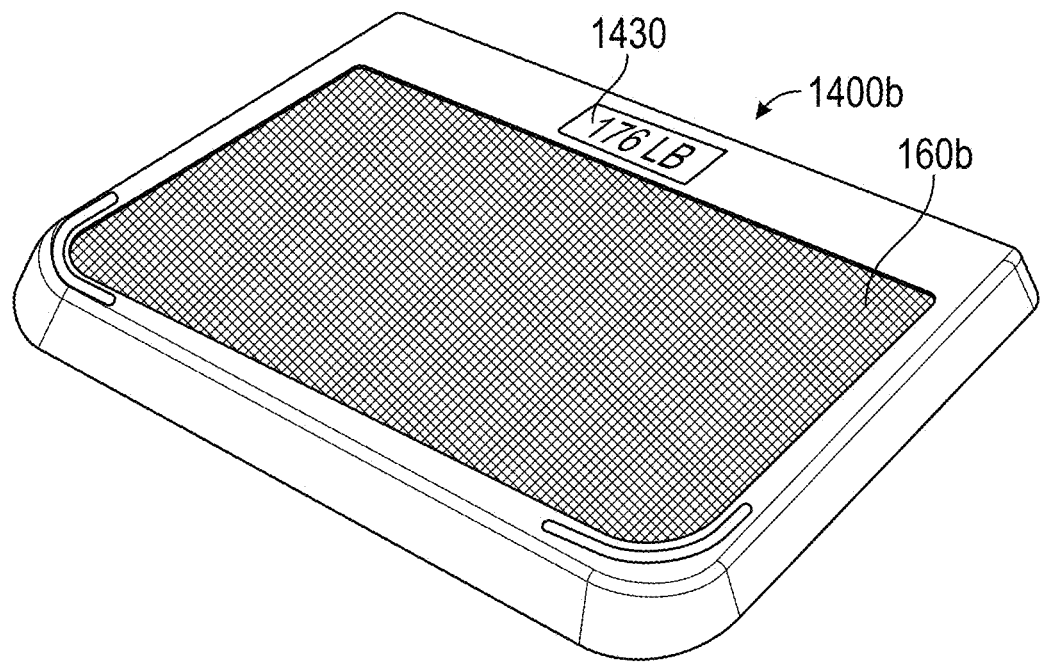
FIG. 21B shows a schematic of a platform of a foot complication detection system configured to perform multiple functions, including a scale for measuring a patient's weight, a foot and leg imager, and a bathroom mat.
Figure 24:
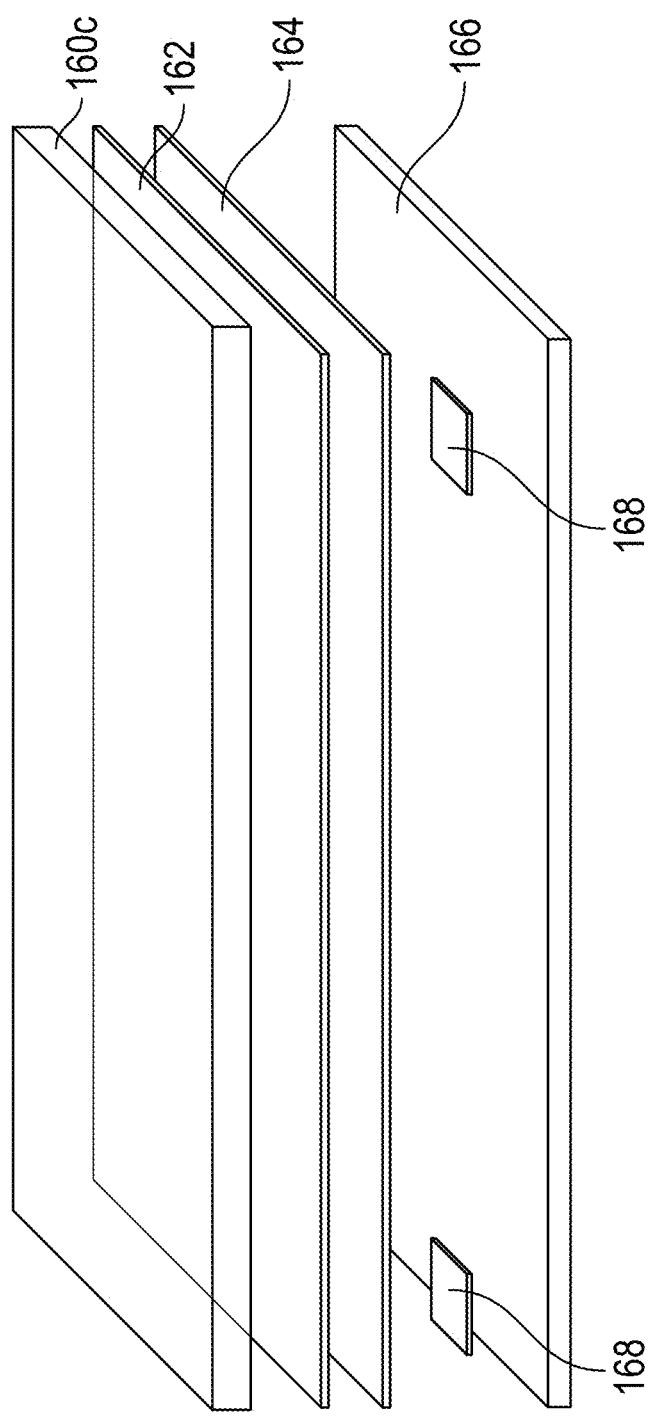
FIG. 24 is a schematic illustration of an exploded view of a foot complication detection platform.

Referring to FIG. 24, in some embodiments, an imaging device (or any other imaging device or system described herein) can include a large area imaging sensor 162, e.g., an imaging sensor that is configured as a two-dimensional array of photodetectors where the size of the sensor is the same as the size of the field of view. The large area imaging sensor can be positioned (e.g., immediately) below the horizontal surface 160c of the platform 100 on which the user stands. The large area imaging sensor can be positioned above support 164 of the platform 100. The imaging device in FIG. 24 also includes one or more than one (2, 3, 4, 5, 6, 7, 8) force transducers or load cells 168 that may rest upon support 164. This and other imaging devices described herein may contain one or more than one large area imaging sensor with these and other features described herein (e.g., each imaging device can be configured as a two-dimensional array of photodetectors where the size of the sensor is the same as the size of the field of view; positioned (e.g., immediately) below the horizontal surface, etc.) Surface 160c on platform 100 may include a protective, non-slip surface, such as made from a polyvinyl chloride (PVC) or a thermoplastic rubber (TPR) material. Surface 160c may be textured, such as with bulges, dots, indents, lines, or waves that prevent a patient from slipping and falling. For example, FIG. 21A shows platform 1400a with surface 160a with textured lines, and FIG. 21B shows platform 1400b with surface 160b with a checkered surface. Any of the surfaces (e.g., surface 160a, 160b, and/or 160c as well as associated structures including image sensors and support materials) can be a continuous surface or discontinuous surfaces. In some examples, a discontinuous surface may have two separate surface regions and act as a foot guide for a patient's feet. For example, FIG. 21A shows separated surface 1438a and surface 1438b configured to separately act as foot guides for placement of a patient's left and right feet. FIG. 22 shows a first large area image sensor 1442a and second large area image sensor 1442b. The image sensors are located under the regions upon which a patient will step. Thus, in some examples, the sensors can be smaller, easier to manufacture, less expensive, allow a more flexible or foldable mat, etc. Load cells 168 on platform 100 can be configured to convert compression or pressure into an output signal. Load cells 168 may be useful as presence sensors or, when a platform is also used as a scale, for determining a patient's weight.

In some embodiments, the large area imaging sensor may advantageously not require the use of lenses for magnification or minification of the field of view. Further, the large area imaging sensor can advantageously complete imaging in less than 30 seconds, such as less than 10 seconds, such as in less than 5 seconds, such as in 3 seconds or less, such as in 1 second or less, advantageously requiring the user to spend only a short amount of time on the platform 100 while still enabling detection of foot complications.

Figure 17:
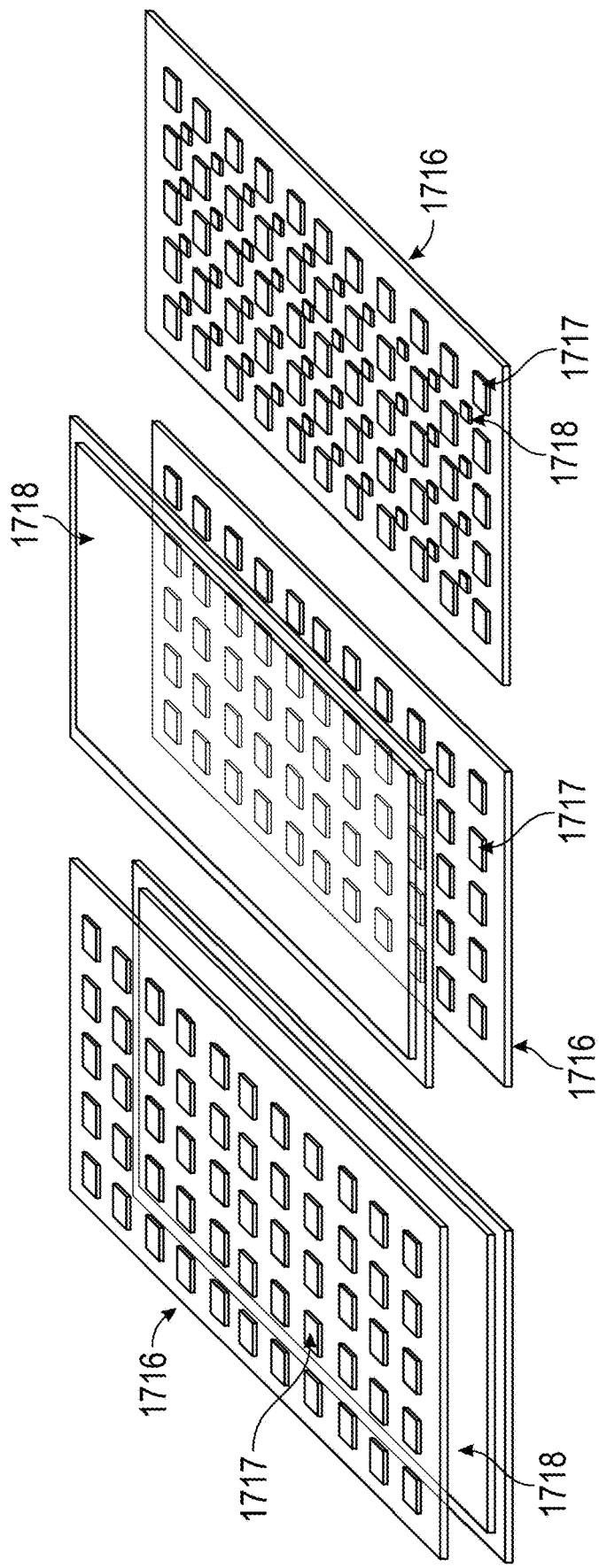
FIGS. 17A-17C show exemplary large area imaging sensors.

Referring to FIGS. 17A-17C, a large area imaging sensor (e.g., large area imaging sensor 162) can, for example, include an array 1716 of photodetectors 1717 that are positioned over a plurality of lighting elements 1718 (e.g., LEDs or other lighting source) and/or a single lighting element 1718 (e.g., a single backlight (e.g., LCD)). Further, the lighting element 1718 for the platform 100 can advantageously be placed below the array 1716 (as shown in FIG. 17A), above the array 1716 (as shown in FIG. 17B), or within the array 1716 (as shown in FIG. 17C). In some embodiments, the large area imaging sensor can include a filter (e.g., red, green, blue) placed over each photodetector 1717 to ensure a given photodetector 1717 only measures a specific wavelength/color of light. In other embodiments, each photodetector 1717 can be configured to be sensitive to a specific wavelength or color light. Using a filter over each photodetector 1717 or having each photodetector 1717 be sensitive to a specific wavelength can advantageously reduce exposure time. In other embodiments, the lighting element 1718 can be configured to emit a specific wavelength or color of light, which can advantageously reduce the number of photodetectors 1717 required for a given pixel resolution.

In some embodiments, the large area image sensor may be made from one or multiple (e.g., 2, 3, 4, 5, or more) wafer-scale image sensors and the sensors may be butted together or may not be butted together (e.g., they may be separated). In some embodiments, the photodetectors may be discrete components mounted to a printed circuit board. In some embodiments, the large area image sensor may be made, for example, from amorphous silicon deposited onto a substrate (e.g., amorphous silicon deposited onto a substrate and selectively crystalized into a polycrystalline silicon or amorphous silicon deposited onto a substrate and without being selectively crystalized into a polycrystalline silicon), or from other organic semiconductor materials. In some embodiments, the substrate of the large area image sensor can be a thin glass substrate. In this embodiment, a rigid transparent window can be placed above the large area sensor and/or a rigid support can be placed below the large area sensor (e.g., with the large area sensor sandwiched therebetween) to help avoid flexing of the large area image sensor. In other embodiments, the substrate of the large area image sensor can be a flexible (e.g., plastic) substrate, which can advantageously help prevent the large area imaging sensor from breaking even under high user loads.

The large area imaging sensor can include a tailored imaging depth such that areas within 75 mm, such as within 50 mm, such as within 40 mm are in focus and areas further away are not in focus. Imaging within this range can ensure that the entire foot can be in focus in the image while preventing privacy concerns by otherwise focusing on more of the patient's body than necessary. A longer imaging depth could be an issue since the imaging can be performed and/or is designed to be performed (in the bathroom) while a patient is undressed, showering, using the toilet, etc. In some embodiments, the large imaging sensor can include a collimator filter therein or thereover to achieve an imaging depth within the tailored range. The collimator, for example, can be fabricated with carbon nanotubes, with a traditional flat panel manufacturing method, or via micro-machined holes (e.g., with a precision laser cutter). In other embodiments, additional lenses can be used with the large area sensor to achieve an imaging depth within the tailored range. These additional lenses can be, for example, micro lenses, gradient-index lenses, and/or composite lenses made from laminated pieces of materials with different indexes of refraction and placed over the photodetectors of the large area imaging sensor.

Advantageously, the large area image sensor can be less than 20 mm, such as less than 10 mm, such as less than 5 mm, such as less than 3 mm, such as less than 2 mm thick. Additionally, the large area imaging sensor can acquire images quickly (e.g., within 10 seconds, within 10 seconds to 1 second (e.g., within 1 second, within 2 seconds, etc.), within 1 second to 0.1 seconds) of the user stepping on or otherwise engaging with the platform). In some examples, an imaging sensor herein (e.g., large area imaging sensor) can acquire images faster than other imaging modalities can, such as other non-sensing modalities (e.g., contact temperature sending) or a moving scanner imaging sensor. Moreover, the large area imaging sensor can advantageously gather images from a wide range of angles and positions (e.g., rather than requiring the user to stand directly on specific imaging windows).

Figure 25A:
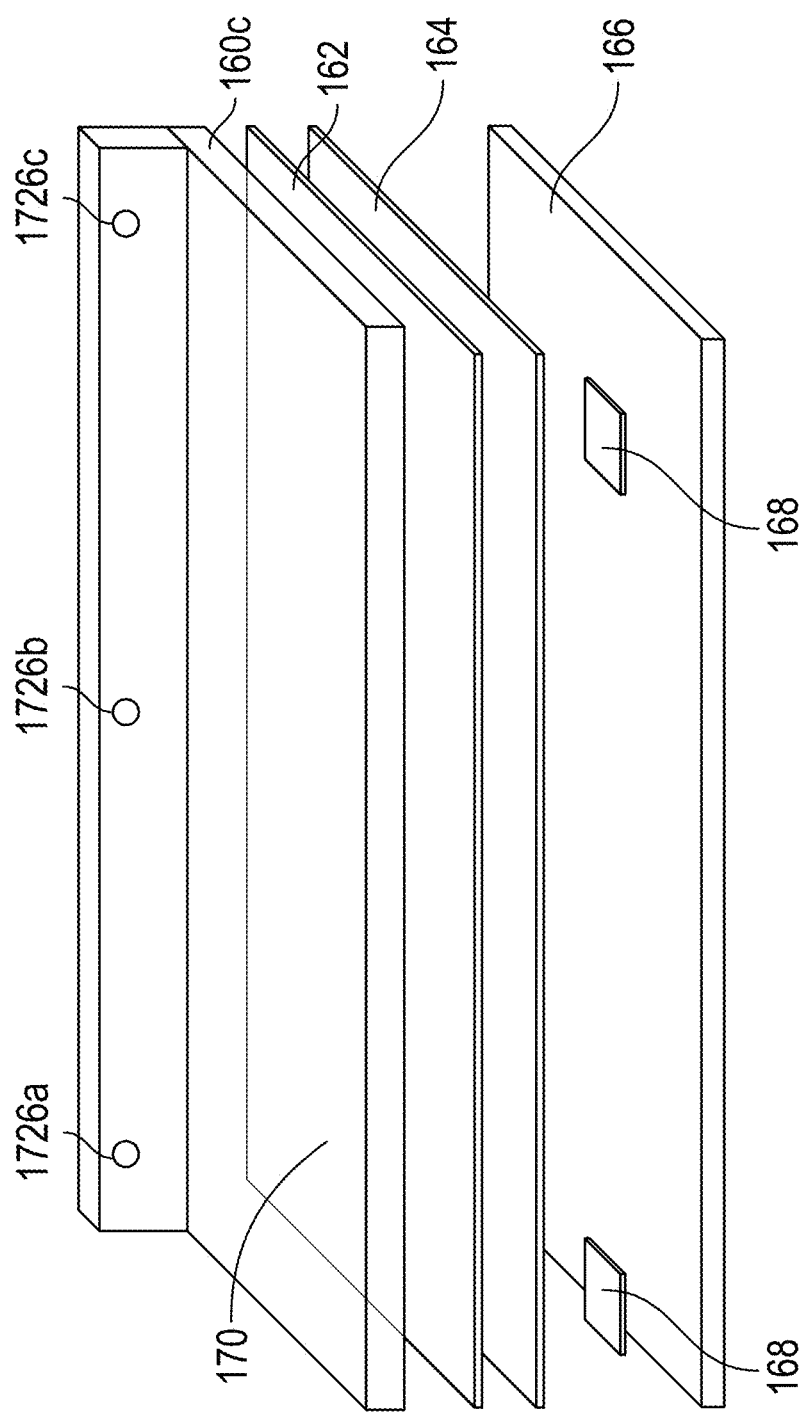
FIGS. 25A-25B are schematic illustrations of an exploded view of a foot complication detection platform with a plurality of side-facing cameras.
Figure 25B:
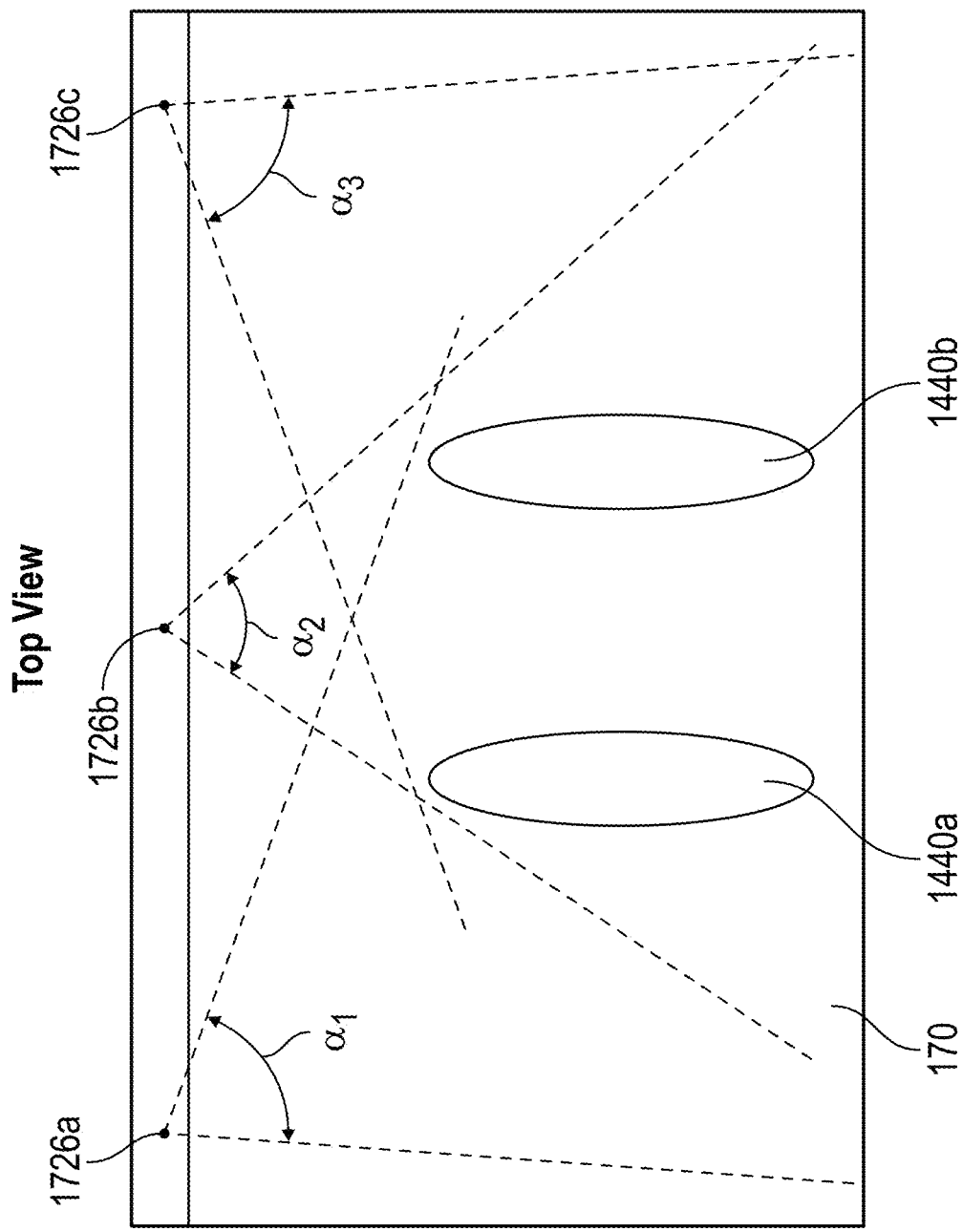

Referring to FIGS. 25A-25B, in some embodiments, the imaging device can include one or more additional cameras positioned on a first vertical or raised side 172 of the imaging device (e.g., above a plantar imaging surface 170). A vertical or raised side may also house electronics for the device. The one or more additional cameras may be in addition to or, in some examples, instead of, the plantar large area imaging sensor 162. FIGS. 25A-25B show, for example, three wide-angle cameras strategically positioned to capture different perspectives on the foot or feet of the patient and may do so simultaneously or sequentially. Other numbers of cameras can also be used and/or placed on other surfaces, such as other side or vertical surfaces. Representative foot placement is shown in first foot location 1440a and second foot location 1440b. (See also FIG. 22). The wide-angle camera lens can capture, for example, from 60° to 180°, such as from 60 to 100, from 100 to 150, from 150 to 170, or from 170 to 180. The wide-angle camera lens can produce a rectilinear image. In some examples, the wide-angle camera lens can be an ultra-wide-angle lens, such as a fisheye lens and may produce a circular rather than a rectilinear image. For example, if the heels are closest to the camera, first camera 1726a captures a region indicated by angle α1, such as the left medial foot from the posterior up to and including the toes, the right lateral foot from the posterior up to and including the toes, the left heel, and the right heel. The second camera 1726b, in turn, captures a region indicated by angle α2, such as the left medial foot from the posterior up to and including the toes, the right medial foot from the posterior up to and including the toes, the left heel, and the right heel. Finally, the third camera 1726c captures a region indicated by angle α3, such as the left lateral foot up from the posterior up to and including the toes, the right medial foot from the posterior up to and including the toes, the left heel, and the right heel. A single camera may image one or more of the plantar aspect of a foot, the heel, the lateral aspect of the foot, ankle, or leg, medial aspect of the foot, ankle, or leg, or any of the toes. Together, however, these cameras can provide stereo images that can be used to generate a 3D model of a user's feet (e.g., by employing measurements made in two or more images taken from different positions).

Non-plantar foot ulcers (typically presenting 5-6 times less frequently than plantar foot ulcers) tend to be concentrated on the toes and heel. In some examples, 3D models create a representation of the toes and/or heels of the patient's feet. The design of the device can keep these areas in view of the stereographic cameras during intended use. In some examples, the cameras (e.g., camera 1726a, camera 1726b, camera 1726c) are in fixed locations on imaging device 104 (and/or relative to one another), and the fixed locations of the cameras is known a priori. Having fixed locations can obviate the first step of many photogrammetric pipelines: registering images to determine real-world positions of the cameras. In some variations, one or more additional cameras may be positioned along a second raised side, a third raised side, or a fourth raised side and/or along a bottom of a top surface of the imaging device (e.g., above the top of the foot). Although described with reference to imaging device 104, any system or imaging device described herein may employ one of more additional cameras positioned on e.g., a vertical or raised side or top side thereof.

In some embodiments, the imaging device 104 can include, in addition to or in lieu of the large area imaging sensor, a linear array of photodetectors (e.g., a contact imaging sensor), a plurality of lights, and one or more scanners. The scanner(s) can move the photodetectors along the full length of the foot to produce the image. In other embodiments, the imaging device 104 can include one or more camera sensors with one or more corresponding lenses. In some embodiments, these camera sensors can be manufactured via wafer-level optics processes, which advantageously may allow them to be made more cheaply, more precisely, and in a smaller size.

The imaging device 104 can be designed to fit within a small vertical space, such as 20 cm or less, 10 cm or less, 5 cm or less, 3 cm or less, 2 cm or less, or 1 cm or less.

In some embodiments, the processor (e.g., platform processor 105 or remote processor 222) can build a visual model of the surface of the patient's foot based upon images gathered by the imaging device 104 and can detect one or more irregularities in the visual model.

Figure 18:
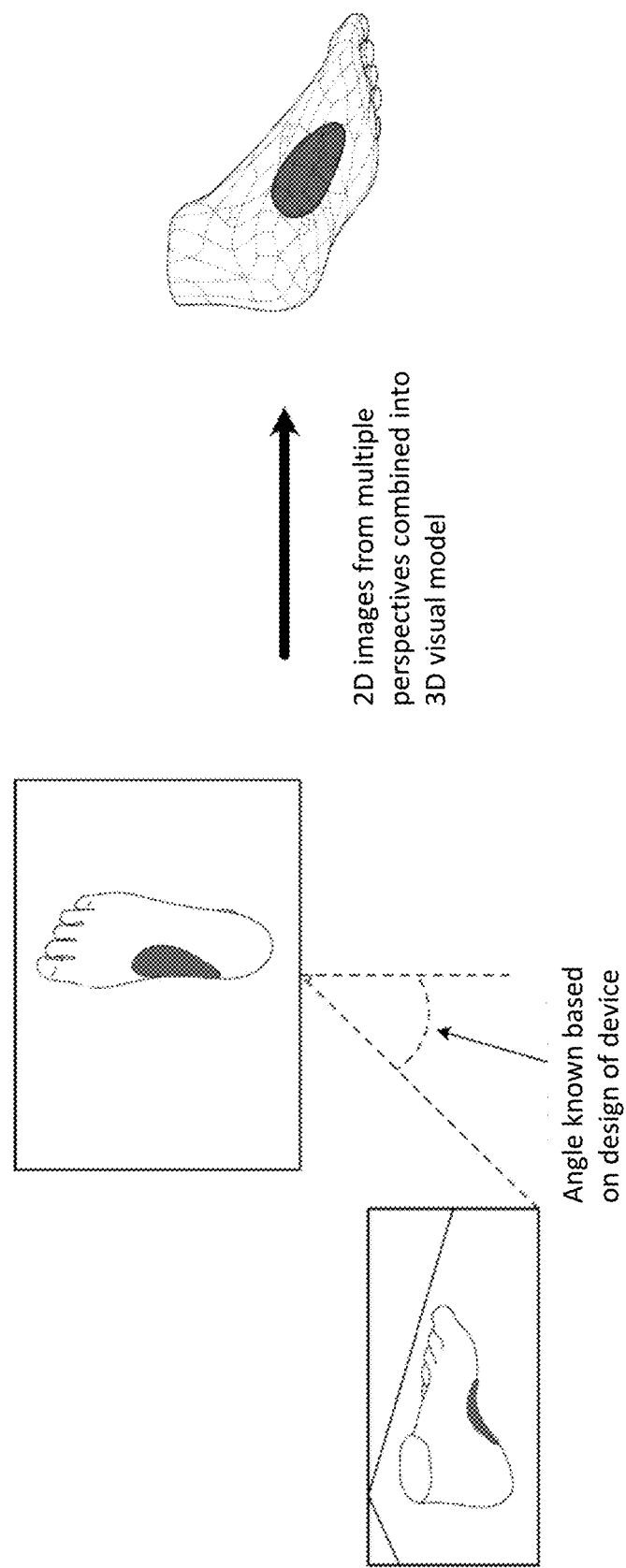
FIG. 18 is a schematic showing production of a 3D visual model of a foot from a plurality of 2D images.

Referring to FIG. 18, in some embodiments, the visual model can be developed by combining all of the images taken by the imaging device 104 to generate a three-dimensional (fully complete or partially complete) visual representation of the surface of the foot, which can then be analyzed for irregularities that may correspond with foot abnormalities or other complications. For example, a visual model can be developed using images from the plantar surface (e.g., with the large area imaging sensor) and from the anterior, posterior, lateral, dorsal, and/or medial surfaces of the foot (e.g., with one or more wide-angle cameras). The images from the anterior, posterior, plantar, medial, lateral, and dorsal perspectives, and/or from any other perspectives, taken during one session (e.g., at the same time or slightly spaced apart temporally) can be associated with (or stitched) together. Image identification from the plantar images can allow the orientation and position of the foot to be determined (e.g., can enable identification of the outline of the foot, the location of the foot on the mat, and/or which way the heel and toes are pointing) in order to create a rudimentary foot model located in virtual 3D space. The side images (which can utilize depth information from a previous calibration, stereo information, geometrical perspective with calibration markers on the board, or other range-imaging methods such as time-of-flight and structured/coded light), in turn, can be used to apply further visual information to the relevant surface of the foot model, based on the associated position and orientation from the plantar images.

In some embodiments, as a patient moves around on the mat, images can be taken continuously and/or at regular intervals. Taking images continuously and/or at regular images can enable the visual model of the patient's foot to be incrementally updated. This incremental updating can advantageously produce a higher resolution three-dimensional visual representation of the foot than the sensor resolution would allow for individual images.

In some embodiments a neural network deep-learning-based approach can be used to generate the 3D models. For example, a Volumetric Regression Network can be used and may advantageously not require the use of a 3D Morphable Model. In some embodiments, a semi-global matching algorithm can be used to compute a disparity map for image pairs, providing depth information. This map can then be used to reproject the images onto a 3D point cloud.

Figure 19B:
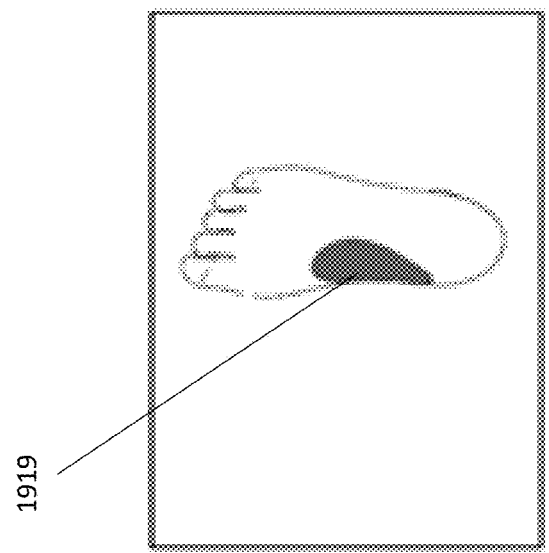
FIGS. 19A-19B are schematics showing different types of image generation.
Figure 19A:
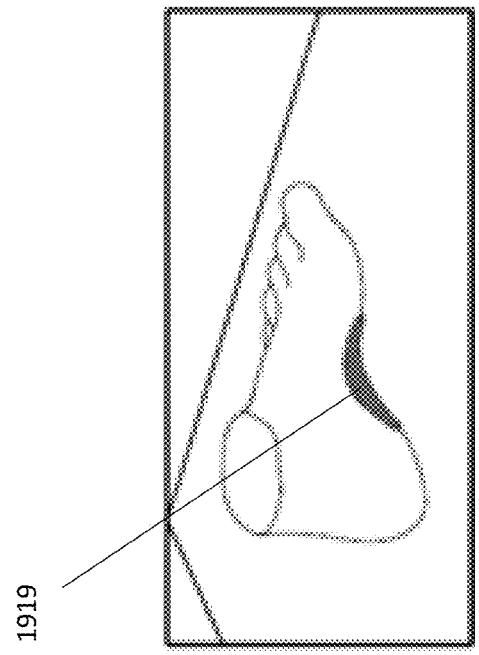

In some embodiments, as shown in FIGS. 19A-19B, the visual model can be developed by tagging the images taken by the imaging device 104 with location and position information of the foot in each of the respective images, allowing a single image view to stand on its own during analysis for foot complications (e.g., enabling analysis with an imaging device that includes only a large area imaging sensor for imaging the plantar surface). That is, by using a plantar image (shown in FIG. 19A), a bare model of the foot can be located and oriented in 3D space. Then, as shown in FIG. 19B, the side image can be mapped directly onto the surface of that model, as the distance from the imaging device 104 to the boundary of the 3D model is known. In the images shown in FIGS. 19A and 19B, there is an ulcer 1919 that spreads from the medial to plantar surfaces because each image is tagged with the position and location information of the foot as the images are taken. In some examples, plantar images can be used without side images and/or without a 3D model to e.g., identify foot structures and foot abnormalities. For example, one or more than one plantar image can be analyzed to identify e.g., toes and heel so that the plantar abnormalities are associated with a location on the plantar surface of the foot.

Figure 20:
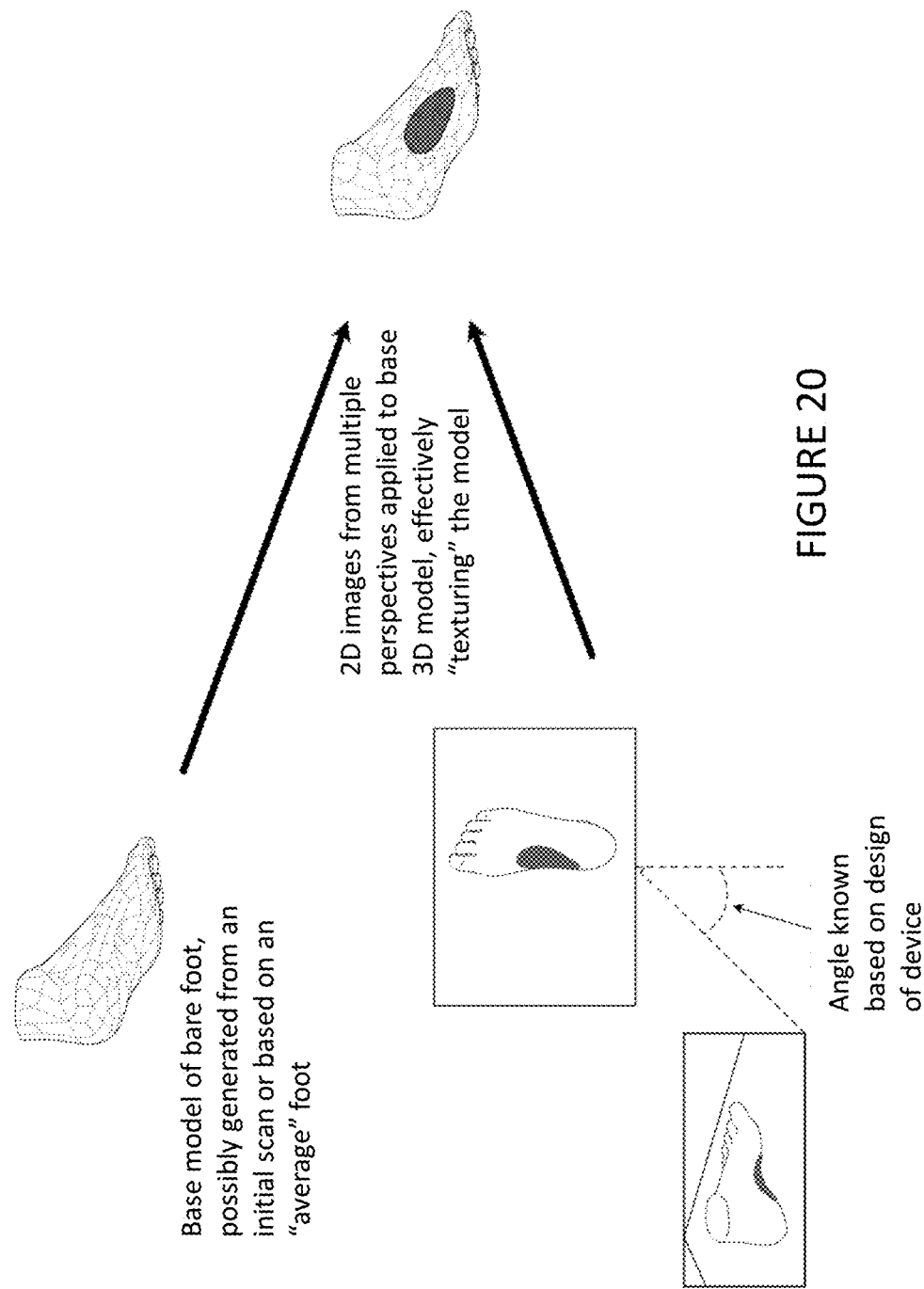
FIG. 20 is a schematic showing production of a 3D visual model of a foot using a 3D model of a standard foot as a basis.

In other embodiments, as shown in FIG. 20, a three-dimensional model of a standard foot can be used as a basis for creating the visual model with the images from the imaging device 104.

In some embodiments, as described above, the visual model can be developed using images from the plantar surface and from the anterior, posterior, medial, dorsal, or lateral surfaces of the foot. In other embodiments, an incomplete visual model can be developed using images from the plantar surface of the foot only.

The irregularities identified by the platform processor 105 or remote processor 222 in the visual model can include, for example, a visual irregularity in a single visual model at a given point in time (e.g., a black spot corresponding to dried blood or necrotic tissue, redness from erythema, a white spot corresponding to a callus, a series of discolored lines indicating fissures from dry skin, or a discoloration under the toenail indicating fungus). The irregularities can include, for example, a difference in the visual model from one point in time compared with another (e.g., the color of a certain spot on a foot changed significantly from week to week, and the discoloration has grown for two days in a row). In some embodiments, the continuous and/or regular images can be used in a time-lapse analysis and/or presentation of the foot (e.g., to determine how a foot complication spread, healed, or otherwise changes over a period of time). Any of the images referred to herein can be black and white images (grayscale) or color images and any of the analyses referred to herein can be performed using black and white images (grayscale) or color images.

Figure 23:
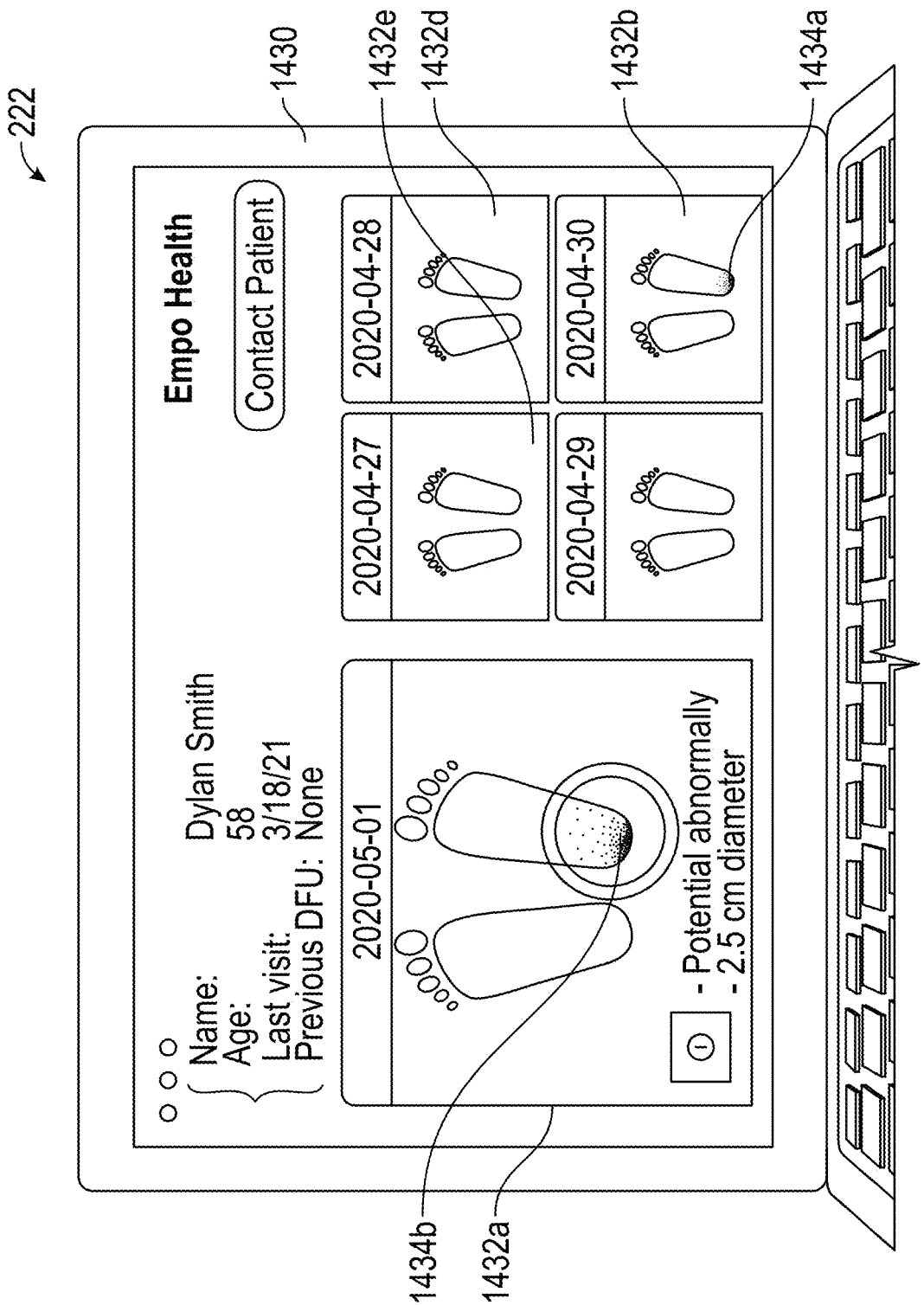
FIG. 23 is a schematic illustration of part of an automatic foot complication detection system comparing a series of images of a patient's feet over time. The series shows progression of a potential foot abnormality over time.

Referring to FIG. 23, remote processor 222 includes display 1430. Display 1430 displays patient information 14 and a series of images 1432a, 1432b, 1432c, 1432d, and 1432e of a patient's feet over time. FIG. 23 shows image 1401a of patient's foot 101 with a 2.5 cm diameter potentially abnormality 1434b. FIG. 23 also shows image 1432b of patient's foot 101 taken just prior to the image 1432a. As shown in FIG. 1432b, the potentially abnormality 1434a has started to develop, but is smaller or less severe than shown in FIG. 1432a. Moreover, the abnormality 1434a/b was not visible in earlier images (1432c, 1432d, and 1432e). By comparing images over time, a care provider can determine various characteristics such as how long a potential abnormality has been on a foot, if the potential abnormality has changed over time, how the potential abnormality has changed over time, how quickly it has changed, if the color of the potential abnormality has changed, etc. Images, such as those illustrated in images 1432a, 1432b, 1432c, 1432d, and 1432e can be automatically generated and analyzed using the systems, devices, and methods described herein. Using the systems, devices, and methods described herein can include the step of displaying a series of images taken over time of the foot of the user on a remote (and/or local) display, wherein a first image of the series of images includes an image of the foot having the foot complication and a second image of the series of images includes an image of the foot not having the foot complication.

One exemplary automated method for analyzing images is through image segmentation/region detection. Clinically relevant information can present in the form of changes in color of a region of the foot and/or changes in size of those regions. Examples of changes include: a red spot appearing or growing in size across multiple days which may indicate e.g., a region of spreading inflammation; a region of red color shrinking in size may indicate e.g., healing; a region of black color appearing or growing in size may indicate the presence of necrotic tissue and other colors on a region of a patient's foot, such as yellow, could indicate an infection; etc. Provided herein are systems, devices, and methods for taking images across different points in time, automatically annotating the images with regions of interest highlighted, measuring the size of a region of interest, and comparing a size and color from the same region with previous images. These systems, devices, and methods may help care providers and clinicians better understand how different (foot) complications may be progressing.

To detect regions of interest, several processing steps can be used. In one exemplary method of detecting regions of interest, first, images can be color corrected to, for example, account for environment effects (e.g., lighting) on image color or minor manufacturing variations across the different photodetectors in an image sensor. Image sensors can be calibrated against known targets during manufacturing (such as in a factory), and color calibration targets can also be included on the platform (mat) to allow for live color correction in the field during platform or mat use.

Once images have been color corrected, segmentation algorithms, such as thresholding, clustering, and/or neural network based algorithms, can be used to identify regions of the photo image that correspond to feet. Once images have been segmented to identify foot regions, images can be screened to separate out or remove any unusable or partial images.

Next, the size and shape of a foot in an image can be used to identify whether it is a left or right foot and/or whether it belongs to a user in question (as opposed to another user). Users can be filtered out, for example, by weight data from load sensors if included in the mat, but analyzing the images of feet directly can provide a level of redundancy. Once regions in images have been fully segmented and identified, these regions can be aligned with other images in a given capture session, as well as with images from other points in time. This approach can allow images to be analyzed not just alone, but also in comparison with other images.

Finally, foot regions from images can be processed with finely tuned image segmentation algorithms to identify regions of interest on the feet. These regions of interest can then be analyzed for e.g., size, average color, color extremes, color gradient direction, etc., and these measures can be compared with other images from other points in time to understand how the regions of interest are changing. Images can be presented to care providers or clinicians with these regions of interest highlighted and associated with the computed metadata (e.g., additional information about the region of interest, such as a size of an abnormality, length of time the abnormality has been visible, how quickly the abnormality is growing (e.g., how quickly the abnormality is doubling in size), how abnormality color is changing over time, time information when different images were gathered.

In some embodiments, the visual model can be combined with infrared images gathered by the platform to provide additional foot complication detection. For example, near-field infrared can be used to determine blood flow and oxygenation, both of which can be used to identify inflammation or peripheral vascular complications. As another example, mid-field and far-field infrared can indicate temperature in order to identify inflammation (high-temperature) or ischemia (low-temperature). Infrared images can be generated, for example, by reflectance spectroscopy (emitting a light and measuring reflectivity/absorbance from the foot), by emission spectroscopy (measuring photon emissions from the foot), or by fluorescence spectroscopy (emitting a light in order to excite specific molecules/compounds in the foot and measuring the resulting photons released).

In some embodiments, the visual model can be combined with pressure distribution information gathered by the platform (e.g., to include weight in the analysis). The pressure distribution information can, for example, indicate a patient's risk of developing a foot complication over time (e.g., because high pressure points can lead to calluses and ulcers). Thus, for example, high-pressure points in the plantar surface of the foot, particularly ones that increase as time goes on, can be flagged as risks for ulcer development. The information can also, for example, be used to identify a complication (for example, a patient's pressure distribution can change with a wound in the heel, as the body compensates). As another example, the pressure distribution can be used to estimate a patient's posture and loading patterns, tracked over time, to identify key changes that may indicate that a patient's musculoskeletal system is undergoing atrophy due to a progression of neuropathy.

Additional exemplary platforms similar to platform 100 are shown in FIGS. 3-16.

Figure 2:
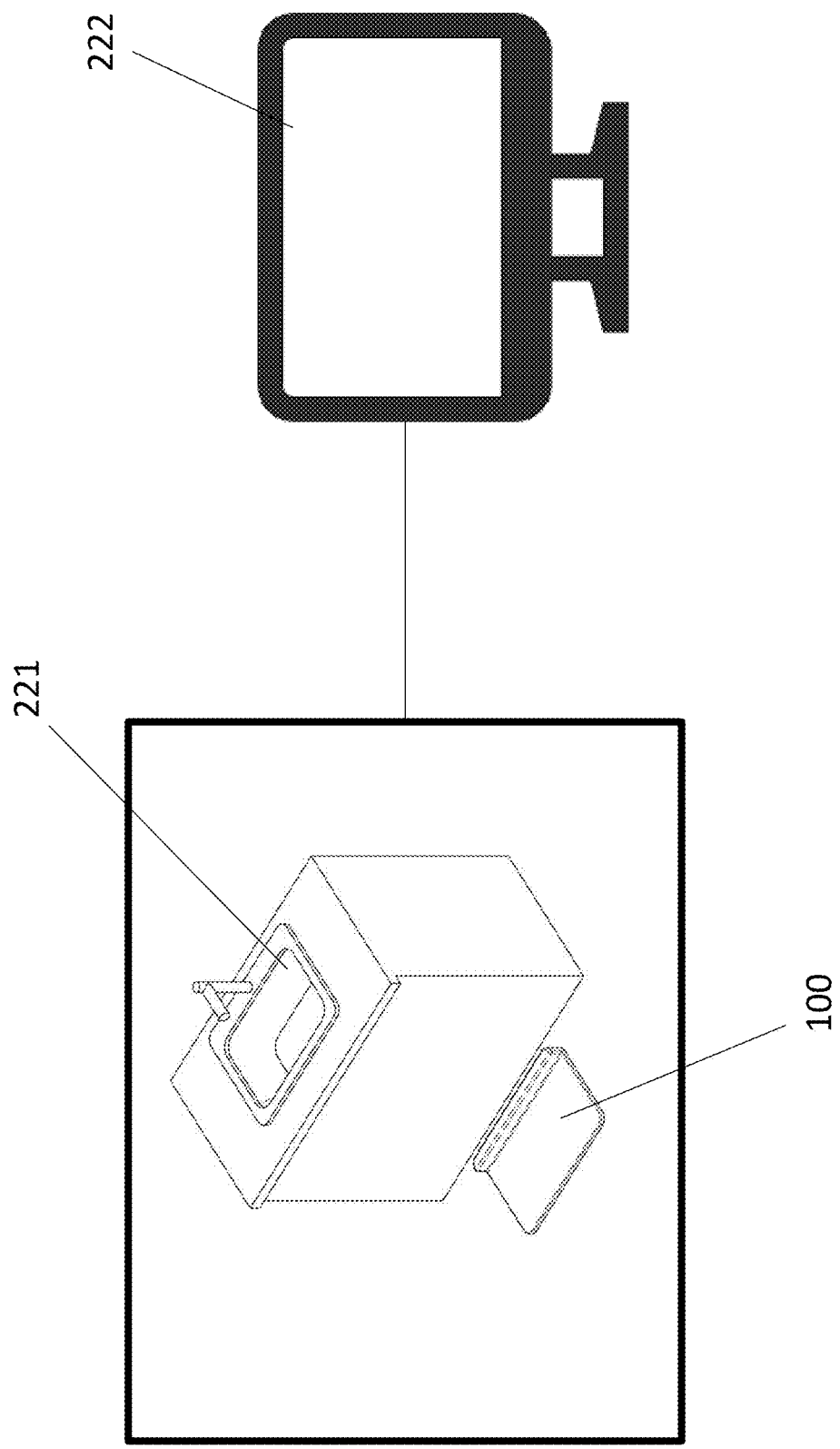
FIG. 2 is a schematic showing an exemplary foot complication detection system.
Figure 4:
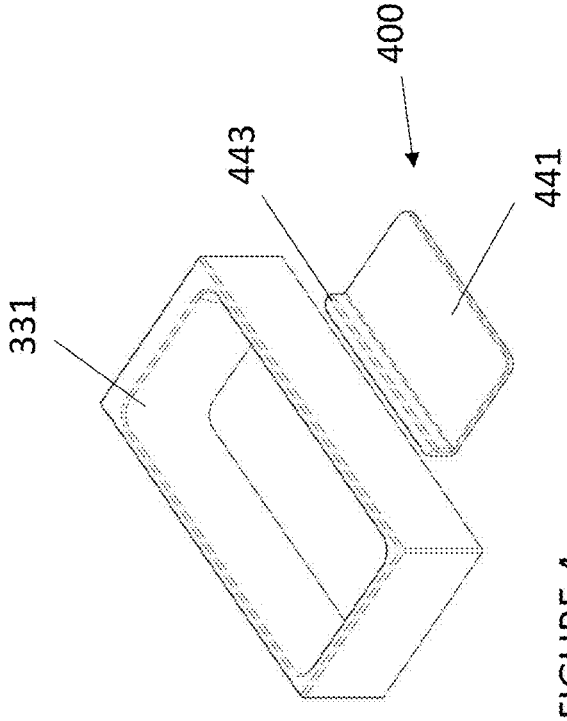
FIG. 4 shows a platform of a foot complication detection system with a raised edge for use near a bathtub.
Figure 6:
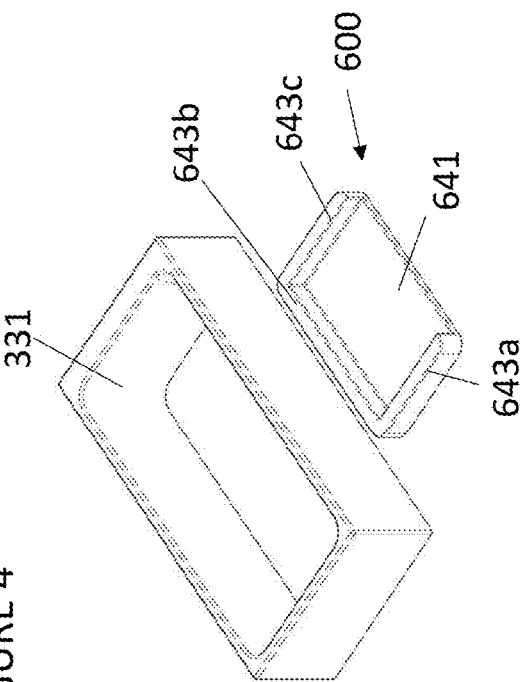
FIG. 6 shows a schematic of a platform of a foot complication detection system for use near a bathtub. The platform has three raised edges for imaging the front and sides of a foot.
Figure 3:
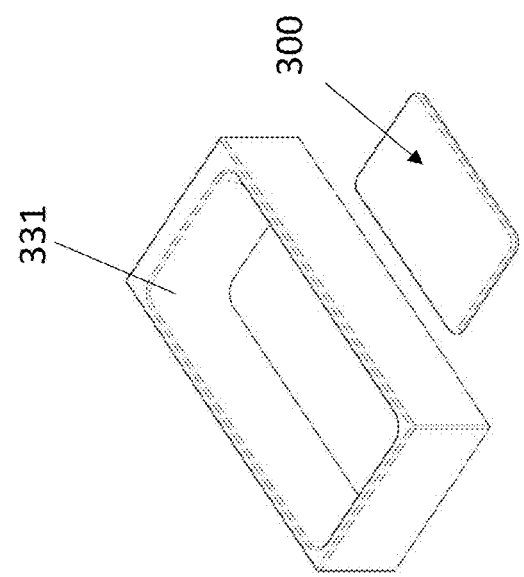
FIG. 3 shows a foot complication detection system for use near a bathtub.
Figure 5:
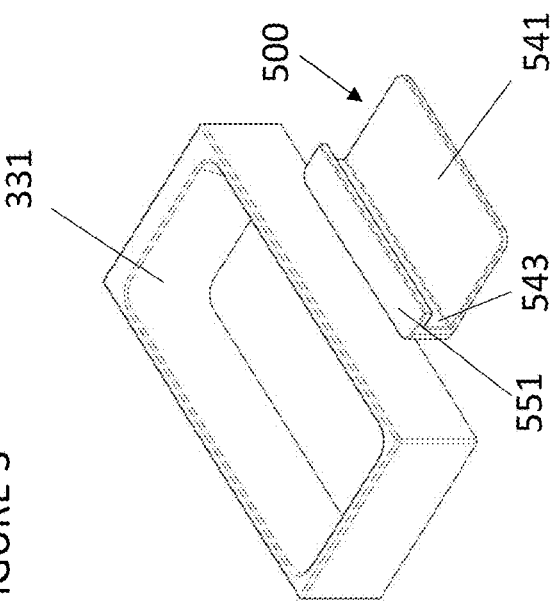
FIG. 5 shows a schematic of a foot complication detection system for use near a bathtub. The platform has an overhang for imaging the top of the foot.
Figure 8:
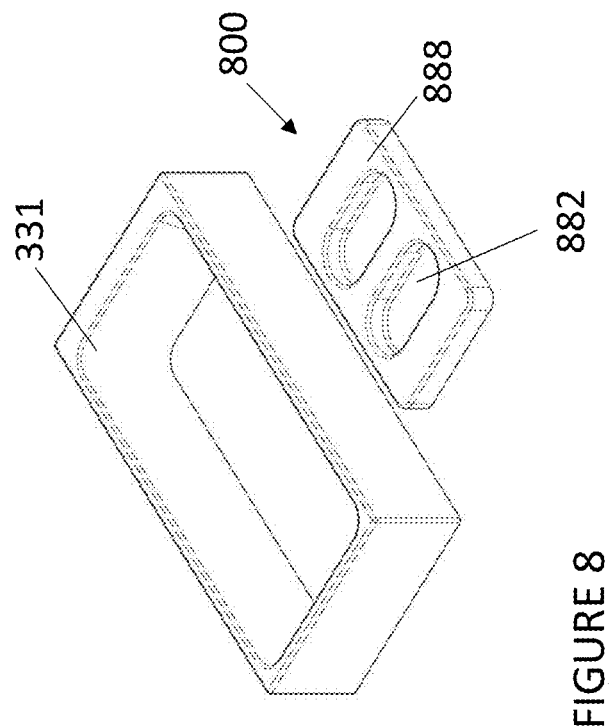
FIG. 8 shows a schematic of a platform of a foot complication detection system with holes or cavities shaped and sized for guiding and receiving a patient's feet into a desired position.
Figure 7:
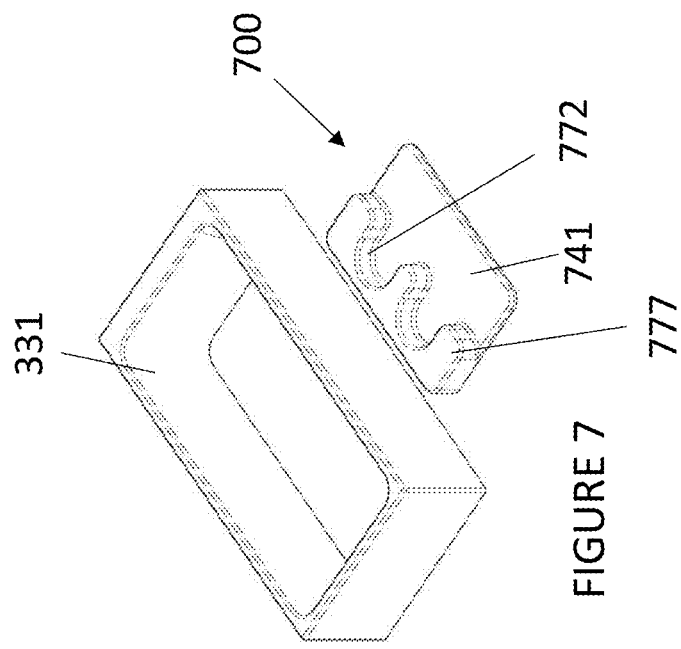
FIG. 7 shows a schematic of a platform of a foot complication detection system with foot shaped cut-outs or contours for receiving the front of a foot.
Figure 9:
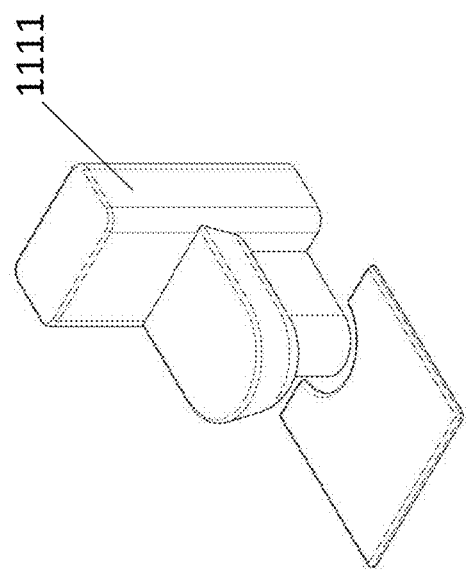
FIG. 9 shows a schematic of a platform of a foot complication detection system configured to sit in front of a toilet.

FIGS. 3-8 show platforms positioned adjacent to a shower or bathtub 331 (though each of the platforms could be positioned adjacent to a sink as shown in FIG. 2 or conforming to a toilet base as shown in FIG. 9). As shown in FIG. 3, platform 300 is a flat mat (e.g., a mat having a thickness of less than 50 mm, such as less than 40 mm, such as less than 30 mm) positioned in front of the shower or bathtub 331. As shown in FIG. 4, platform 400 includes a flat mat 441 with a raised edge 443 that is positioned against the bathtub 331 (e.g., so as to avoid tripping thereover). The flat mat 441 can include an imaging device therein configured to image the bottom of the foot while the raised edge 443 can include an imaging device therein configured to image the front, sides, and/or top of the foot. As shown in FIG. 5, platform 500 includes a flat mat 541 with a raised edge 543 having an overhang 551 to better image the top of the foot. As shown in FIG. 6, the platform 600 includes a flat mat 641 with three raised edges 643*a,b,c* to better image the front and sides of the foot. As shown in FIG. 7, the platform 700 includes a flat mat 741 with a raised element 777 with cut-outs 772 configured to conform to or closely follow the contour of the front of the foot. The raised element 777 can include an imaging device therein configured to image the front, sides, and/or top of the foot. As shown in FIG. 8, the platform 800 includes a flat mat 841 with a raised top layer 888 having holes 882 (also referred to herein as cavities or indents) therein configured to enable the user to stand therein. The holes or cavities extend only partway through the platform or map. The raised top layer 888 can advantageously image all the way around the lateral surfaces of the foot when the user is positioned on the platform 800.

Additional platform designs are shown in FIGS. 21A-21B and FIG. 22. In some variations, any platform as described herein can perform other functions, in addition to performing imaging functions and analysis. For example, platform 1400*a* in FIG. 21A, platform 1400*b* in FIG. 21B, and platform 1400*c* are combined scale and foot complication detectors and include a scale for determining a patient's weight as well as image sensors for detecting a foot complication. The patient's weight may be displayed to the patient on display 1430. A scale may have a piezoelectric transducer that compresses and produces an electric current when a patient steps on the platform 1400*c*. In some variations, display 1430 may display other information, such as an alert flag that indicates the patient may have a foot complication or should seek medical attention. FIG. 21B is additionally configured as a bathroom mat (bath room mat), such as for use outside of a bathtub, shower, or sink.

Figure 10:
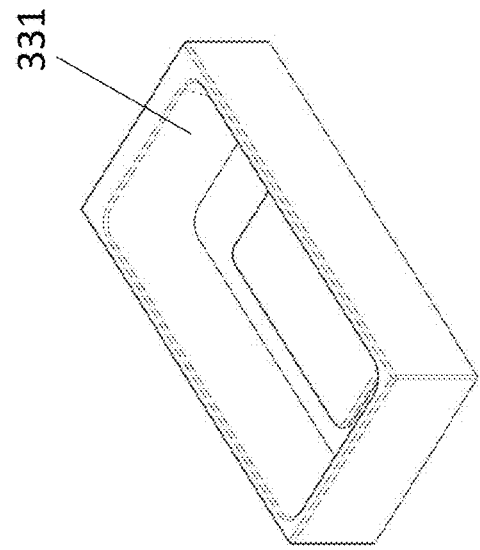
FIG. 10 shows a flat mat platform configured to be placed in a bathtub or shower.
Figure 11:
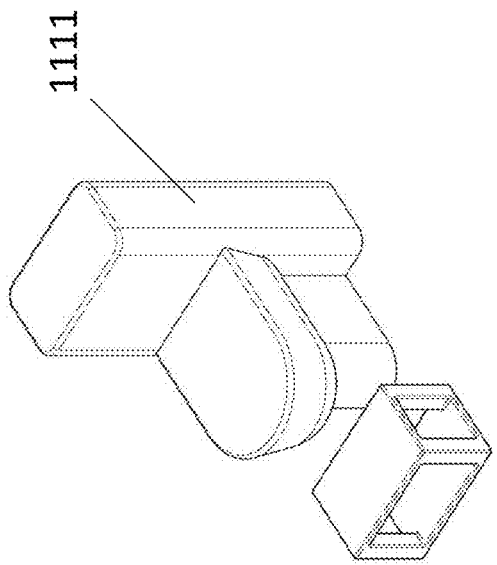
FIG. 11 shows a stool platform of a foot complication detection system in front of a toilet.

Other platform designs are described herein. For example, as shown in FIG. 9, the platform 900 can be a flat mat positioned and/or conforming to the base of toilet 1111. As shown in FIG. 10, in some embodiments, the platform 1000 can be a flat mat configured to be placed in a bathtub 331 or shower. As shown in FIG. 11, the platform 1100 can be a stool configured to be placed in front of toilet 1111.

Figure 13:
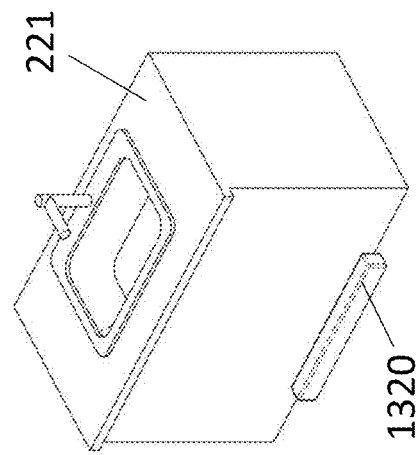
FIG. 13 shows a block element with sensors and imaging devices next to a sink.
Figure 15:
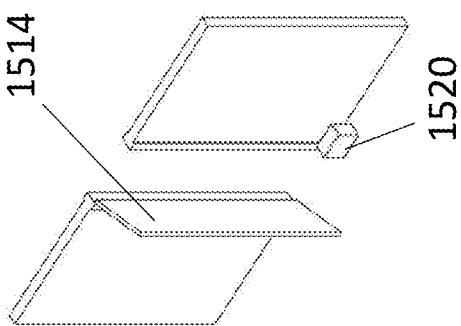
FIG. 15 shows a block element with sensors and imaging devices placed on the side of a bathroom door.
Figure 12:
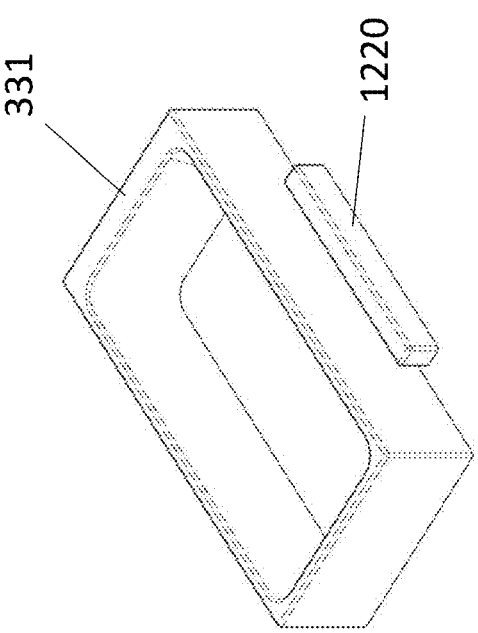
FIG. 12 shows a block element of a foot complication detection system with sensors and imaging devices next to a bathtub. The block element can image a patient's feet without the patient stepping on the block element.
Figure 14:
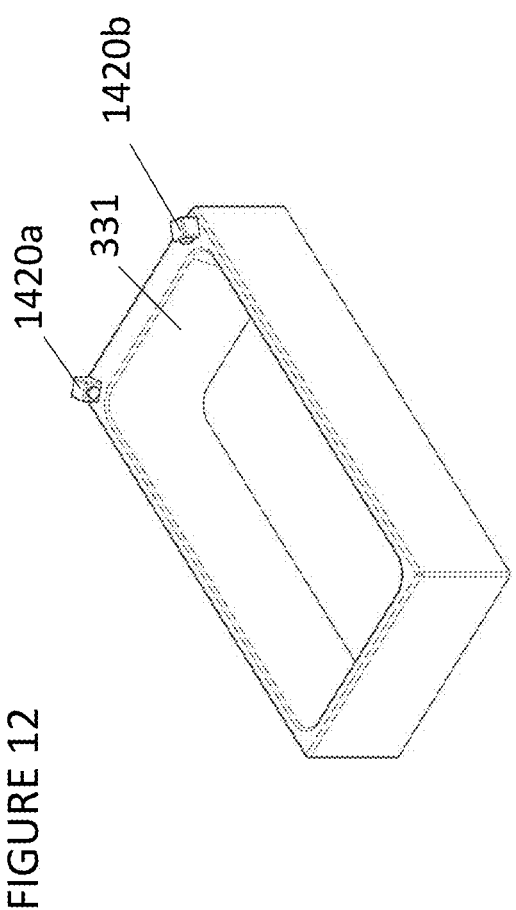
FIG. 14 shows block elements with sensors and imaging devices placed at the corners of a bathtub.
Figure 16:
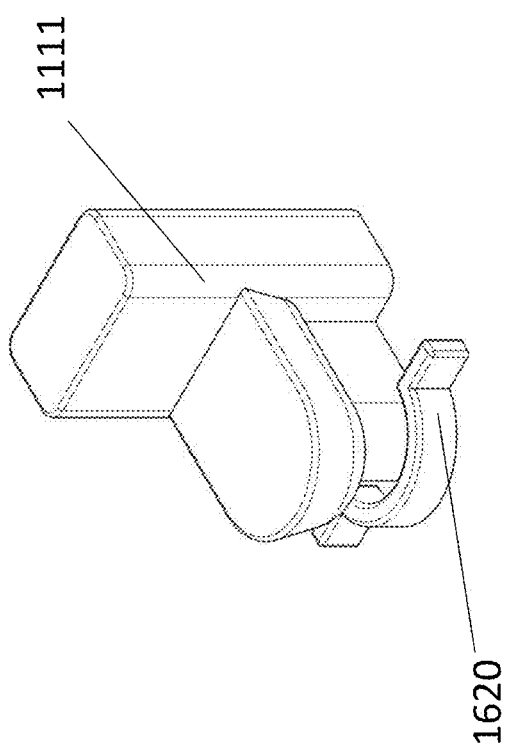
FIG. 16 shows a block element with sensors and imaging devices shaped and sized to partially wrap around the base of a toilet.

In some embodiments, the platform can be replaced with a block element (including the sensors, imaging device, and/or other features of the platform as described herein) that is configured to be placed in the bathroom, but not stepped upon. For example, as shown in FIG. 12, an elongated block element 1220 can be placed next to the bathtub 331. Similarly, an elongated block element 1320 can be placed next to the sink 221, as shown in FIG. 13. In other embodiments, one or more block elements 1420*a,b* can be placed at the corners of the bathtub 331, as shown in FIG. 14. One or more block elements 1520 can be placed on the side of the bathroom door 1514 as shown in FIG. 15. One or more block elements 1620 can be placed around the base of the toilet 1111 as shown in FIG. 16.

Advantageously, the systems described herein can enable passive visual monitoring for foot complications. Passive monitoring (i.e., monitoring that does not require activation or input by an individual, such as the patient) can advantageously help ensure patient compliance. Visual monitoring can advantageously automate the current standard of care for foot complication detection and can provide the user (e.g., the medical provider) with detailed medical information regarding the patient's disease state.

Additionally, the systems described herein can advantageously be placed in the bathroom because, while many patients at high risk for ulcers are told to consistently wear shoes, patients tend to still be barefoot in the bathroom, thereby enabling imaging of the feet and monitoring for foot complications.

Figure 26A:
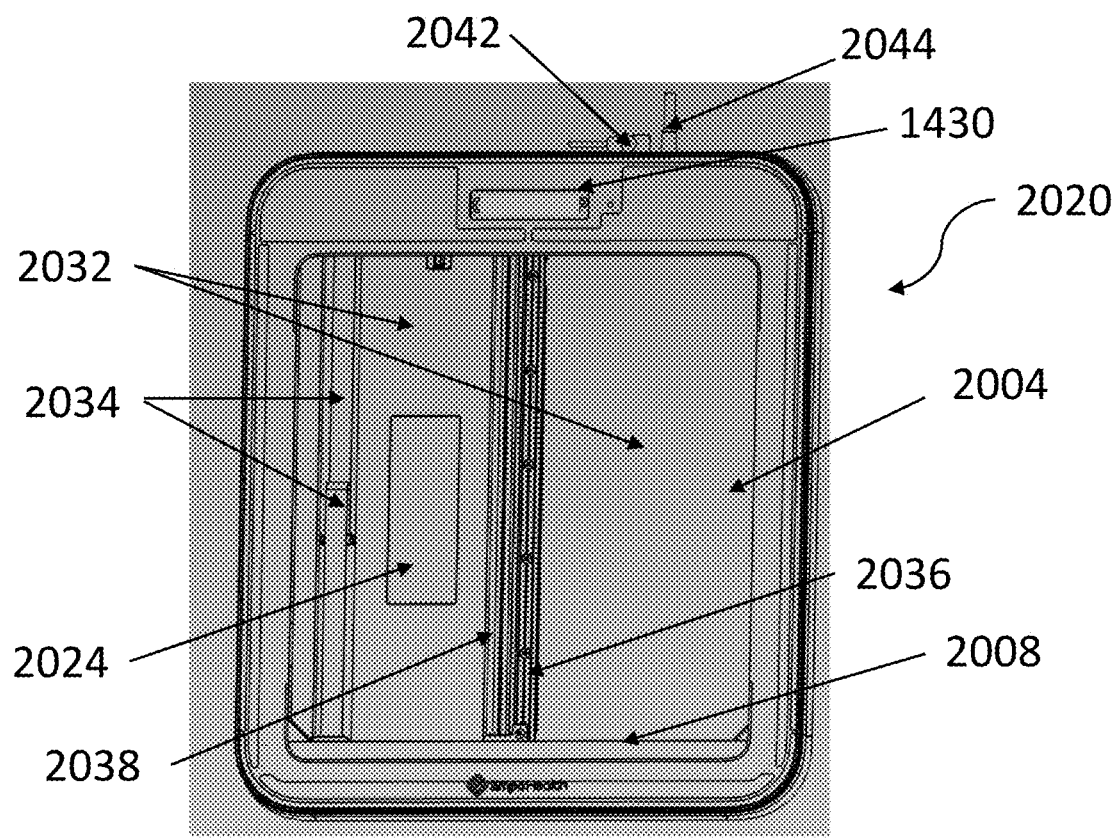
FIG. 26A illustrates a top view of an imaging system.
Figure 26B:
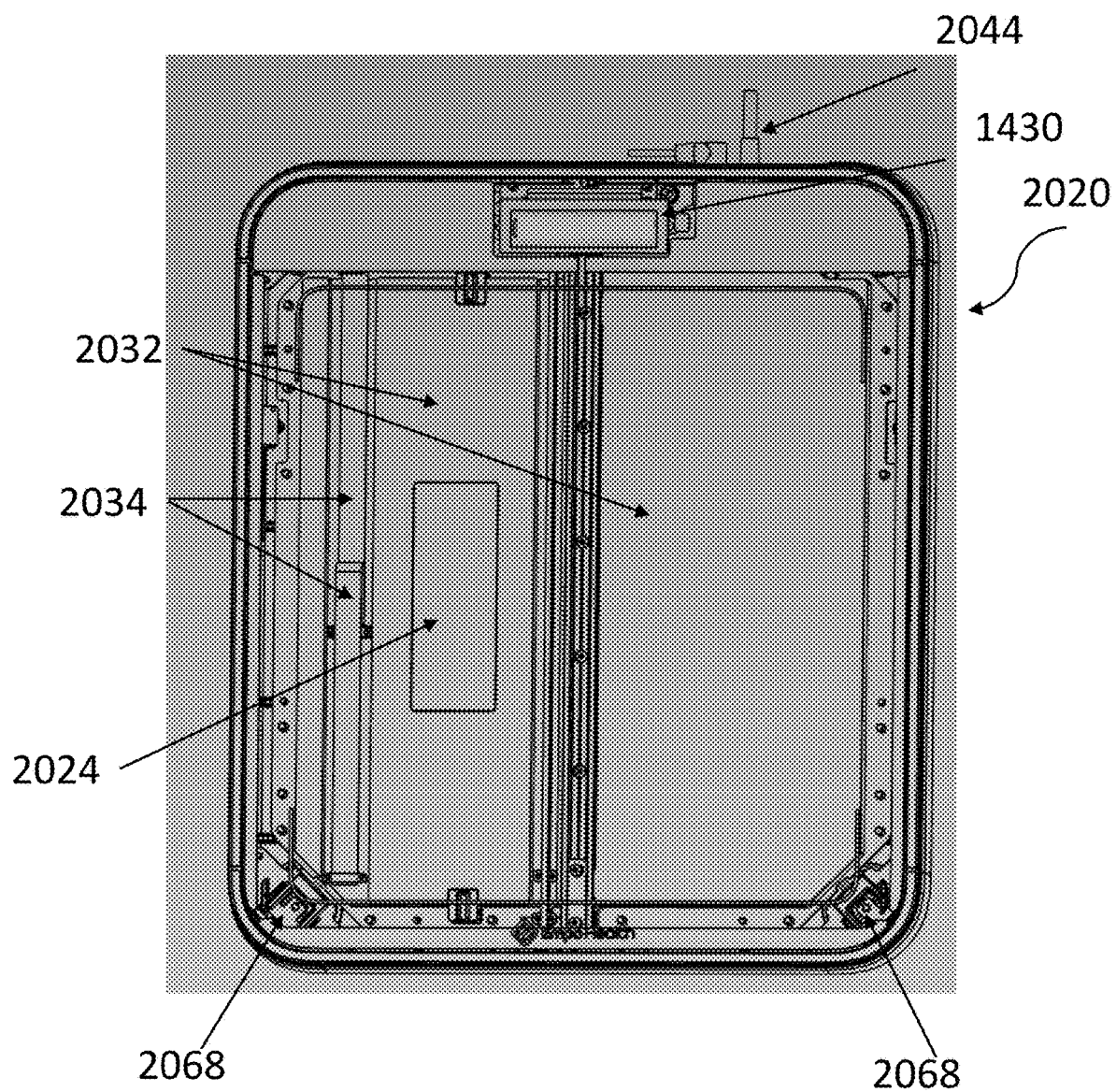
FIG. 26B illustrates a top view of the imaging system shown in FIG. 25A with some of the top component removed to show the inside of the system.
Figure 26C:
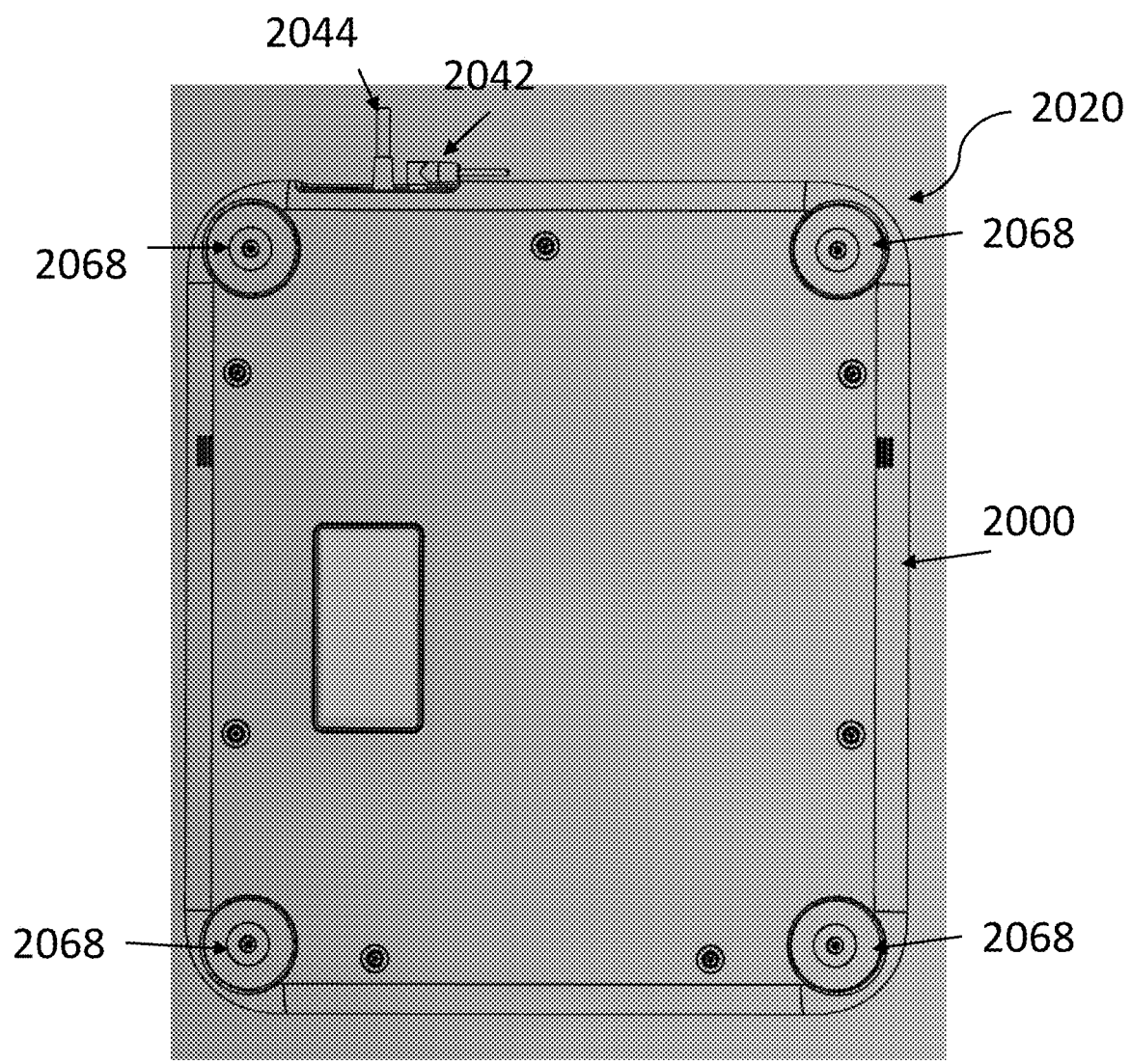
FIG. 26C illustrates a bottom view of the imaging system illustrated in FIGS. 25A and 25B.

FIGS. 26A-26C show another embodiment of a system 2020 for detecting a foot abnormality. System 2020 utilizes a scanning module for imaging a foot. System 2020 includes various features that can work alone or together to enable high image quality, high load capacity (e.g., weight of a user), and a small form factor. FIG. 26A schematically illustrates a top view of system 2020. FIG. 26A illustrates system 2020 including a platform with a top layer 2004, a lower tray 2032, a cable 2034, linear rail 2036, and belt 2038. FIG. 26A also schematically illustrates system 2020 with plate antenna 2040 for WiFi, jack 2042, and USB cable 2044. FIG. 26B schematically illustrates top view of system 2020 with top layer 2004 and part of the housing removed. FIG. 26C schematically illustrates a bottom view of platform 2000 of system 2020 illustrating feet or bottom portions of load cells 2068. FIG. 26C illustrates the four load cells 2068 spaced apart and positioned near the corners of the platform. Although a typical load cell setup, a system 2020 can instead have fewer or more load cells and can be positioned elsewhere.

Figure 27A:
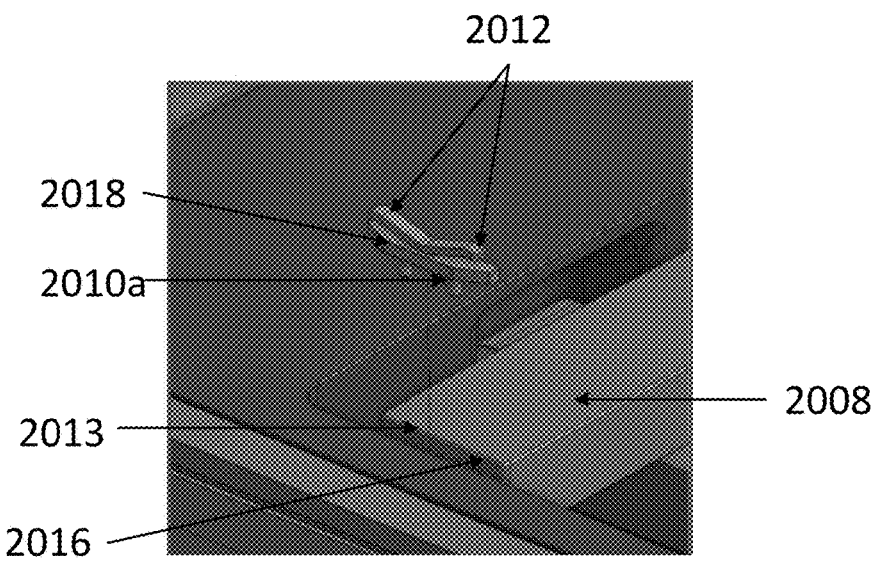
FIG. 27A illustrates a spacer for modulating distance between an imaging device and a top layer.
Figure 27B:
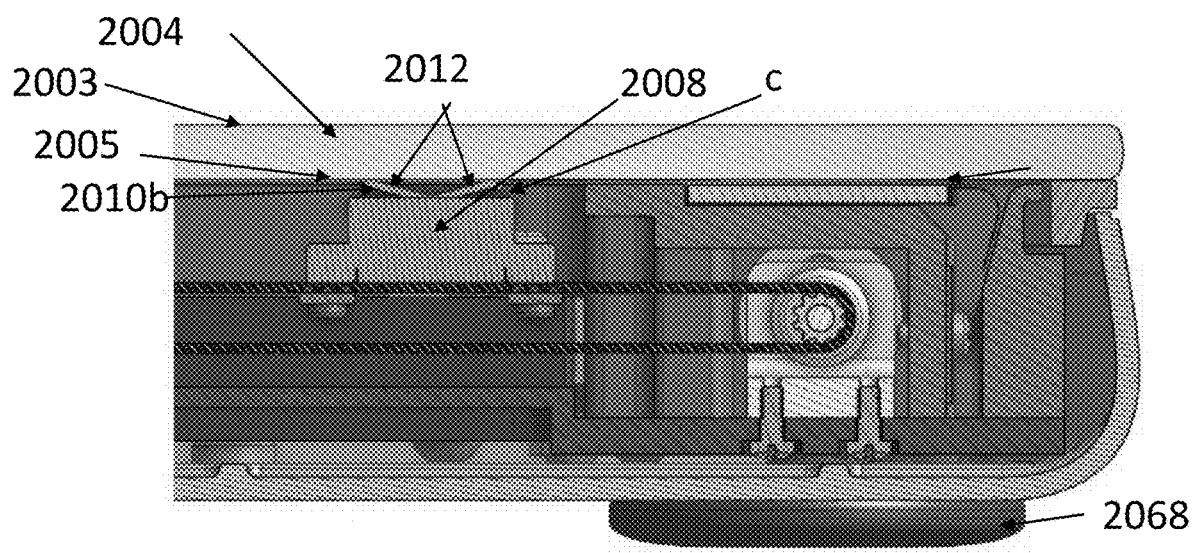
FIG. 27B illustrates a side view of spacer relative to a scanning module.

FIG. 27A-27B schematically illustrate detail views of part of system 2020. FIG. 27A illustrates a top perspective view of a first corner region of system 2020 with some of the top structures, such as top layer 2004, removed to better illustrate structures below it. FIG. 27B illustrates a side cut-away view of a second corner region of system 2020. FIG. 27A-27B illustrate positions of spacers 2010 relative to other components. Spacers 2010 are under top layer 2004 and body 2018 of spacer 2010 is adjacent to scanning module 2008. Dotted line 2013 in FIG. 27A illustrates the position of spacer 2010 in system 2020 when spacer 2010 is in place. FIG. 27A demonstrates that the body spacer 2010 is in the same horizontal plane (e.g., same XY plane as is scanning module 2008, relative to the plane of top layer 2004). Spacer positioning can enable spacer 2010 to perform various functions (discussed in more detail below). FIG. 27A shows spacer 2010 located at outer end 2016 (a first outer end) of scanning module 2008 in the first corner. FIG. 27B illustrates a second spacer 2010 is similarly positioned at the other (second) outer end of scanning module 2008 relative to scanning module 2008.

The pair of spacers 2010 (e.g., in the first corner and the second corner) are configured to work together. For example, FIG. 27B shows clearance c between a top of scanning module 2008 and a second side 2005 of top layer 2004 in the second corner. A similar clearance is present between a top of scanning module 2008 and second 2005 of top layer 2004 in the first corner of system 2020. FIG. 27A also shows a pair of extensions 2012 (also referred to herein as "rabbit ears") of spacer 2010 extending away from body 2018 of the spacer 2010. In FIG. 27A the pair of extensions 2012 extend away from each other in opposite directions, although this is not always the case. In some variations, spacer 2010 could loop, bend towards the middle of the body, etc. A spacer can be a single, monolithic structure, such as spacer 2010 with the pair of extensions. In some variations, a spacer may not be a single monolithic structure.

For example, a spacer could include two structures side by side. In the side view of FIG. 27B, extensions 2012 of spacer 2010 are visible above scanning module 2008. The body of spacer 2010 (adjacent to and in the same plane as scanning module 2008) is not visible in this side view as it is blocked by scanning module 2008. FIG. 27B also shows spacer 2010 contacting lower (second surface) of top layer 2004. The spacers 2010 can be configured to prevent the scanning module 2008 from rubbing against bottom (second side) of 2005 of top layer 2004. Spacer(s) 2010 are able to deflect with the top layer when the scale is heavily loaded, without binding or causing an excess of friction. Spacers 2010 can also (or instead) be configured to prevent scanning module 2008 from becoming non-parallel (e.g., skewed) relative to top layer 2004. By acting to maintain clearance between scanning module 2008 and second side 2005 of top layer 2004, scanning module 2008 can move under top layer 2004 to successively take images of a foot of an individual along a foot length or width. By maintaining light, symmetrical contact with bottom (second side) of top layer 2004, spacer 2010 can act to reduce or prevent unwanted movement (e.g., vibration or oscillation or wobble) of scanning module 2008 during usage, which improves image quality. In some variations, spacers 2010 can work in conjunction with imaging devices that do not move. A system may have just two spacers (i.e., only two spacers) or more than two spacers. A system herein, including but not limited to system 2020, can be subject to a wide range of conditions from different users and in different use cases, and may be configured to adjust to or work with these different conditions. For example, a system herein may be configured to function with a wide range of loads. An individual using a system herein may be standing on a platform (e.g., platform 2000 or any other platform) and may subject the system to their full (or close to full) body weight, which may greater than 150 lbs, greater than 200 lbs, greater than 250 lbs, greater than 300 lbs, greater than 350 lbs, greater than 400 lbs, etc. In other conditions, a system herein may be used for imaging a foot of an individual, wherein the individual is sitting down (or even lying down) during system use. Under these conditions, load on the platform may be less than one or only a few pounds. A system herein can be configured so that scanning module 2008 can image a foot of an individual, in the absence of a substantial load of hundreds of pounds. In this way, a system herein can maintain stable imaging performance even when scanning users of considerable mass. This contrasts with other applications for scanning modules, which perform best when maintained as close to their top glass as possible, and do not have to contend with varying, large loads upon their glass. For example, common application of a scanning module in an office flatbed scanner or a bill scanner within an ATM machine are not subject to varying, large loads and may use, for example, edge spacers of rollers or fixed low friction members with suitable outcomes. In some variations, an edge spacer could include a roller biased by a spring to the top surface. Such a variation may require more space and/or could increase the system's overall size and cost. Such a variation may be suitable for certain applications (such as in a medical clinic). Spacers herein can be produced, by various methods. For example, spacers can be produced from a low-lubricity material, such as a resin for additive manufacturing, such as iglide i3000 (igus, East Providence, Rhode Island).

Figure 28:
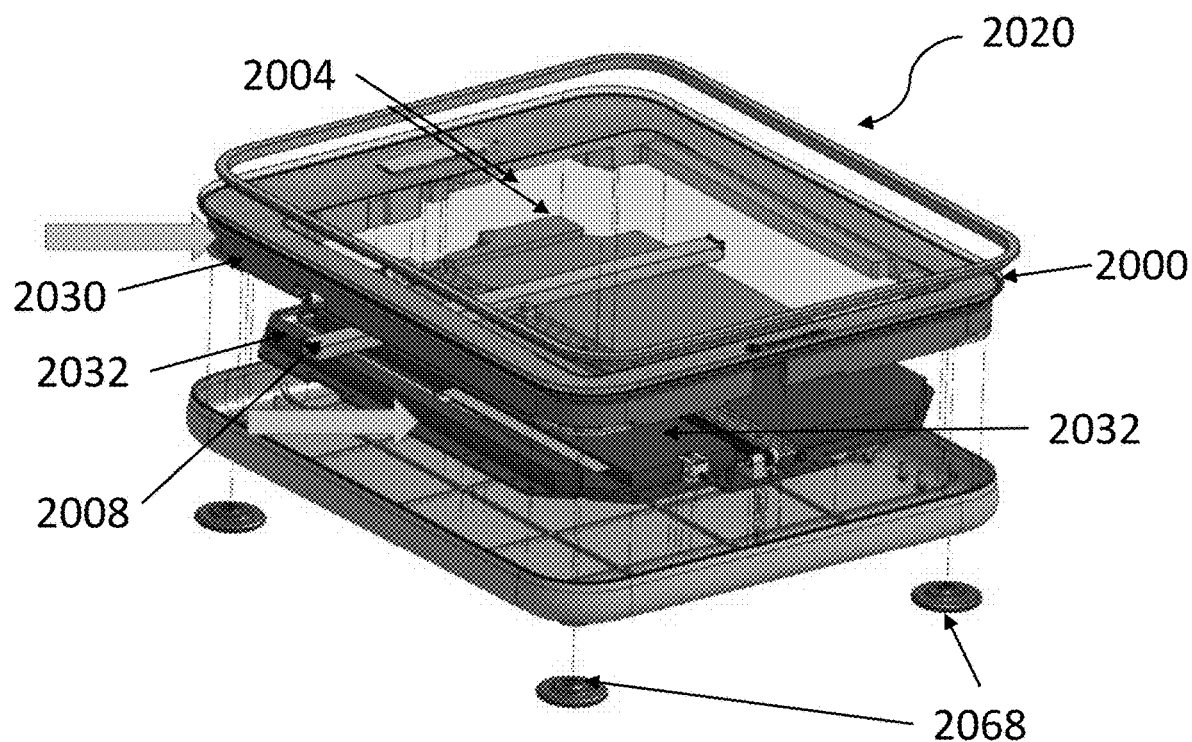
FIG. 28 illustrates an exploded view of an imaging system.

FIG. 28 schematically illustrates a partially exploded view of system 2020. FIG. 28 illustrates system 2020 with platform 2000, top layer 2004, chassis 2032, cover 2030 (may also be referred to herein as cosmetic cover, scanner module 2008 (e.g., between top layer 2004, cover 2030 chassis 2032, system is assembled and not exploded). System 2020 and other systems herein can include a communication module, and can include, for example a radiofrequency (RF) telemetry device, such as for an LTE (Long-Term Evolution) network or WiFi antenna. An antenna may be enclosed within the platform which may be manufactured from a relatively strong and relatively inexpensive metal. This may advantageously prevent breakage and facilitate a relatively small system footprint. However, obstructions (such as e.g., furniture, floors, walls, metal, etc.) weaken RF signals. The system 2020 may typically be used on a floor (i.e., an RF obstructor). System 2020 or other systems herein may typically be used in a small place (e.g., a bathroom) and may abut a structure such as a cabinet, bathtub, wall (i.e., an RF obstructor) during system use. While positioning system 2020 higher in a room (away from a floor) or in a less encumbered location (away from a cabinet, shower stall, or toilet) could help with RF signal processing, such options may not be readily available, at least because an individual typically stands on the platform and, as explained above, may do so in the bathroom as when shoes are not being worn. As indicated above, platform 2000 may be subject to significant loads (including being repeatedly stepped) during regular use. In some variations, a system herein may include system parts manufactured from sufficiently strong, RF transmissive materials. For example, a structural chassis (e.g., chassis 2034), housing and component parts (e.g., cover 2030, such as cosmetic cover, edge, base, etc.) of a system herein can be made of an RF transmissive, reinforced polymer. For example, various system parts can be manufactured in part or in whole as glass-filled polymers, such as glass-filled polyamide/glass-filled nylon parts. Glass-filled nylon typically uses nylon as a base material and adds in short glass fibers to provide strength. Glass-filled nylon combines the strength and mechanical properties of glass with the versatility of nylon. Such materials can be manufactured, such as by additive manufacturing (e.g., 3D printing), computer numerical control (CNC) machining or injection molding. An example of a material is Grivory GV (EMS-Grivory, Via Innovativa, Switzerland). Glass-filled nylon is typically more expensive than metal; however, its other qualities may make it desirable for some applications.

Figure 29:
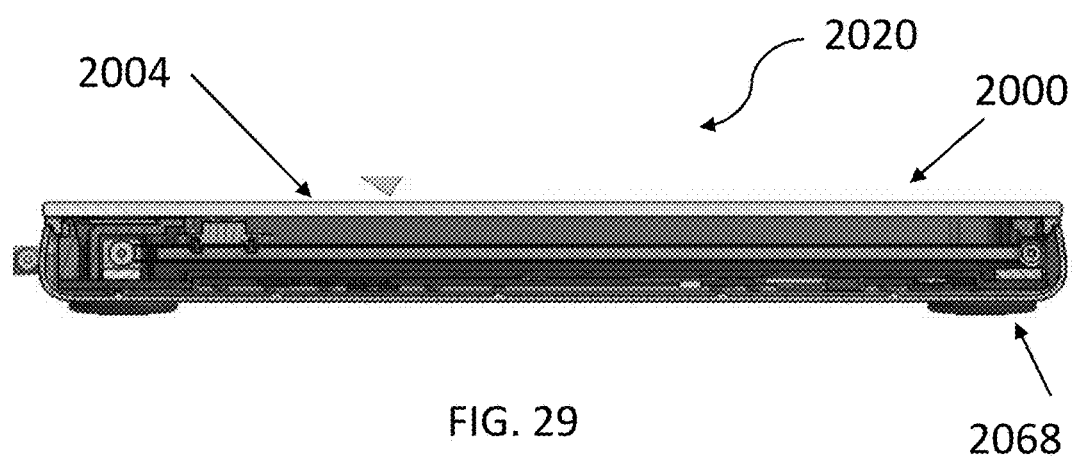
FIG. 29 illustrates a side cross-sectional view of an imaging system.

FIG. 29 schematically illustrates a side cut-away view of system 2020. An individual steps on a first side of top layer 2004 and an individual's foot is imaged through top layer 2004. While materials used on scanners do not typically need to meet these indicators, top layer 2004 may 2004 may preferably meet several performance indicators, such as, to support a patient of up to, for example, 200 kg, and also allow for acceptable imaging performance. Since photons used for imaging a patient's foot go through the glass, its optical properties are of interest. Both the composition of the glass, and also its thickness, affect imaging performance. Additionally, to allow for a scanning area which will fit the vast majority of users' feet, the glass typically holds the body weight (of an individual) over a large, unsupported area. For example, a human foot can exert in the range of 60-80 kPa when walking. Described herein is use of tempered low-iron soda lime glass for forming top layer 2004 or other tops of platforms herein that may be especially useful for its high light transmissivity, mechanical strength, and tendency to form cubic fragments when shattered. In some variations, a top layer of a system herein can be manufactured from laminated "safety" glass. A safety glass can made with one (i.e., only one), two (i.e., only two), or more than two sheets of glass or polycarbonate. For example, a glass can include two tempered low-iron soda lime glass or other optically transparent layers laminated together with an optically clear tie layer (also referred to herein as an interlayer) that has minimal (substantially no) distortion. In some variations, a safety glass can include a single layer of tempered low-iron soda lime glass or another optically transparent layer and a layer of safety film and without a second of tempered low-iron soda lime glass or another optically transparent layer. The layer of safety film can be configured to hold pieces (pebbles) of the optically transparent layer if it should break and to minimize scattering of the pieces (pebbles). The layer of safety film can, for example, be composed of tie or interlayer material. An interlayer can include a polymer, such as a bonding resin, such as polyvinylbutyral (PVB) or a film. Although tempered glass is harder to break than typical inorganic glass, it can break and when tempered glass is broken, the energy therein is typically released all at once and the glass breaks into very small pebbles. While breakage of glass (e.g., in a system herein) is undesirable, safety glass can be safer than typical inorganic glass when it does break, and typically, tempering maintains the optical properties of the glass. Similar as to described above for glass-filled nylon laminated safety glass is more expensive to manufacture than some other commonly available materials, such as glass and specialized expertise is typically required to handle it; however, its other qualities may make it desirable for some applications.

Figure 30:
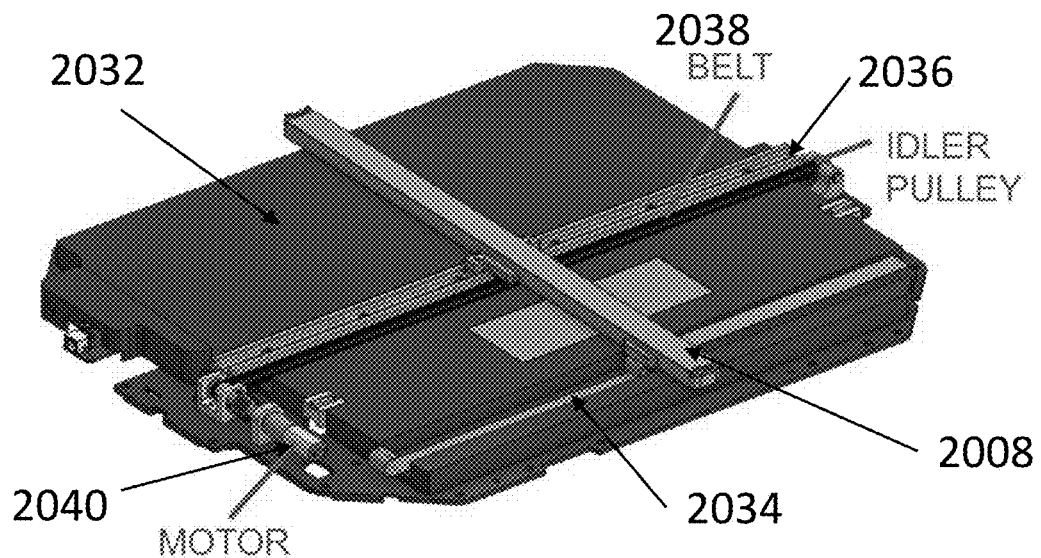
FIG. 30 illustrates a chassis and scanning module of an imaging system.
Figure 31:
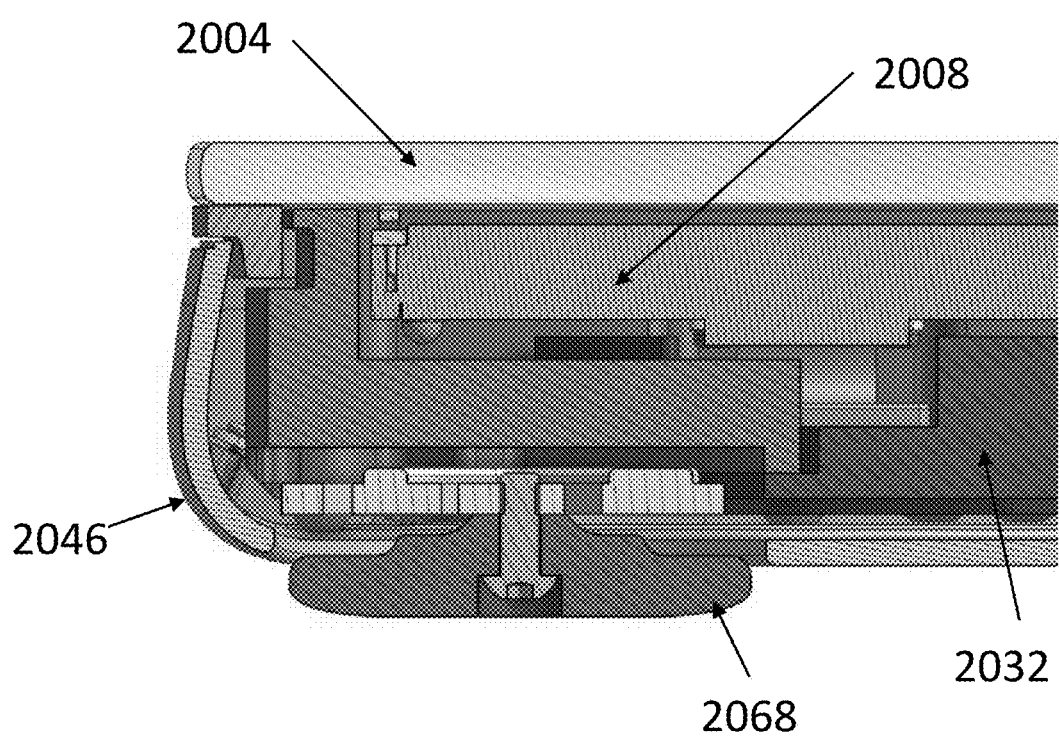
FIG. 31 illustrates a side view of part of an imaging system.

FIG. 30 schematically shows a perspective view of part of an inside of a system, such as of system 2020. Top layers and other structures have been removed to highlight chassis 2032, scanning module 2008, motor 2040, and linear rail 2036. Motor 2040 drives cable 2034 to drive movement of scanning module 2008 along rail 2036. Motor 2040 of the device's scanning system is provided with an encoder, which provides feedback to the motion controller on the system's position (and by extension, velocity). This allows for control (e.g., precise) of the scanhead's motion, specifically for smooth and quick accelerations and decelerations, as well as smooth steady-state motion. When the device's scanning system operates as a line scanner, the sampling interval of the CIS (contact image sensor) scanner is can be tied to the velocity of the CIS module for forming spatially coherent images. To this end, the timing of the scanning element's sampling is tied to the output of the system's encoder. Use of an encoder in this method advantageously allows for the scan to start as soon as motion starts, instead of needing to wait for some steady velocity state to be achieved, as is typically the case. This enables a desirable possible active scanning area within a given device form factor, by eliminating the need for physical space that would be used only for the acceleration and deceleration of the scan head without corresponding scanning taking place. In some variations, another device can be used to move the scan head (e.g., to specific positions) during scan head motion, such as e.g., a stepper motor, etc.

The use of an encoder as a motion control feedback mechanism also allows the device to adapt to changing friction conditions within the device. As a user of considerable mass steps onto the device, it can deflect and warp to some extent. For example, in the case of the top layer (top glass) deflecting into the "rabbit-ear" spacers, the spacers will deflect with a minimum of force, but the change in drag upon the system's motor might cause variations in speed or motion that could adversely affect scanning performance. By driving the scan mechanism in a velocity-controlled mode with encoder feedback, these adverse effects can be hedged. FIG. 30 also illustrates belt 2038 that drives movement of scanning module 2008 from a first end of the platform to a second end of the platform to image a foot/feet of a user. In some variations, use of a belt-drive for the transfer of force from the system's motor to the moving CIS scan head can have several distinct advantages over alternative force transmission options. Firstly, a belt drive system may be far less vulnerable to racking/binding/misalignment than a system based on a gear rack. As such, it allows for the device to tolerate larger strains and therefore larger loads for a given structural rigidity and size, without risking misalignment and binding. Additionally, the belt drive offers a dense vertical packing efficiency, which aids in minimizing the device's thickness. In other variations, other actuators can be used. For example, an actuator for moving a scan head can be a rack and pinion actuator, a cable-driven actuator, a leadscrew actuator, an electromagnetic linear motor (e.g., Javelin™ actuator series, Celera Motion), etc. In some variations, a system herein can include two CIS scan heads, such as, for example, one for each foot. Such a system can include one motor or encoder or can include two (one for each scan head).

Figure 32A:
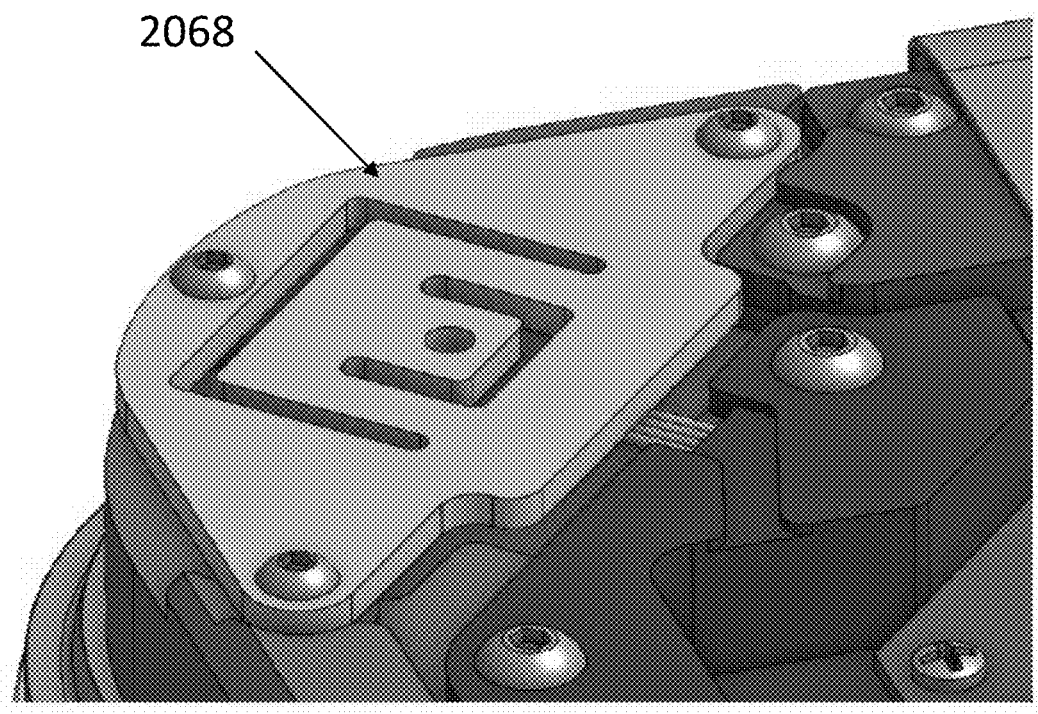
FIG. 32A illustrates a load cell for use in an imaging system.
Figure 32B:
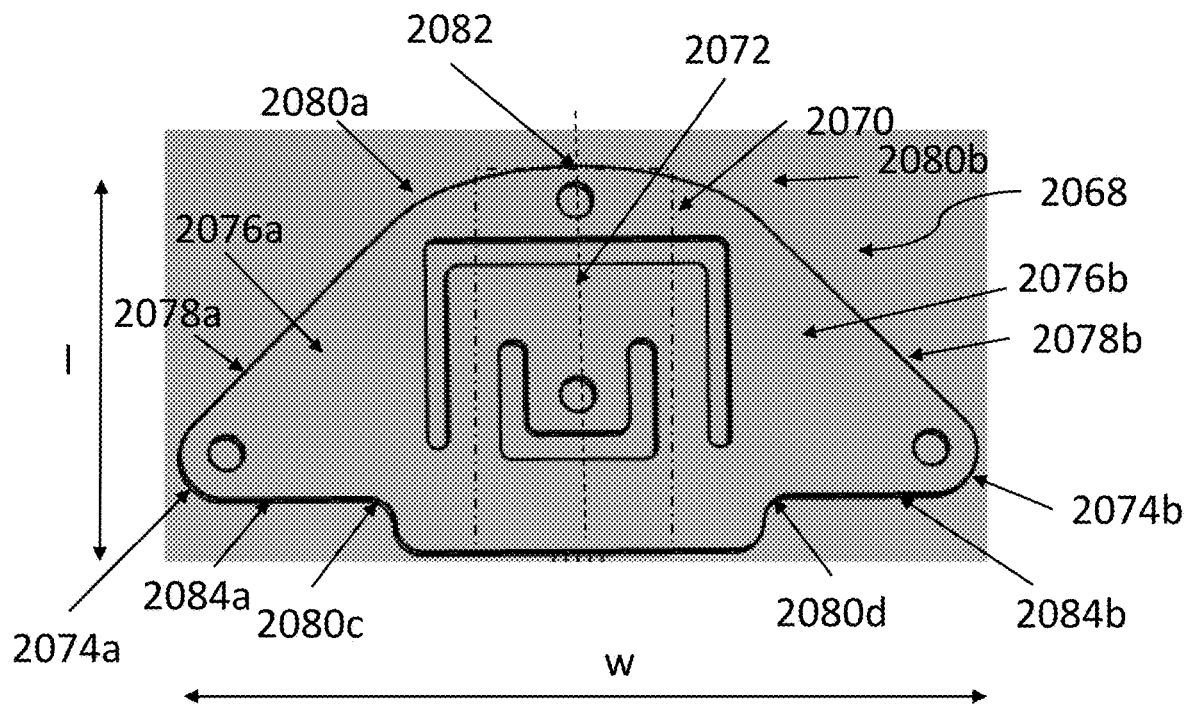
FIG. 32B illustrates another view of the load cell illustrated in FIG. 32A.
Figure 32C:
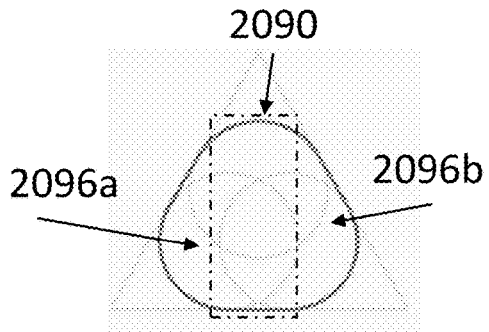
FIGS. 32C-32D illustrate other load cells.
Figure 32D:
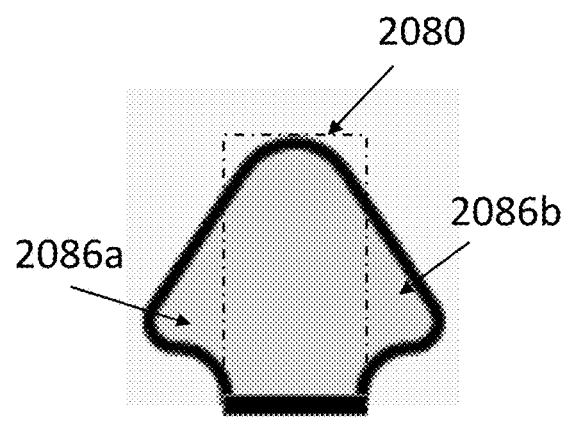
Figure 32E:
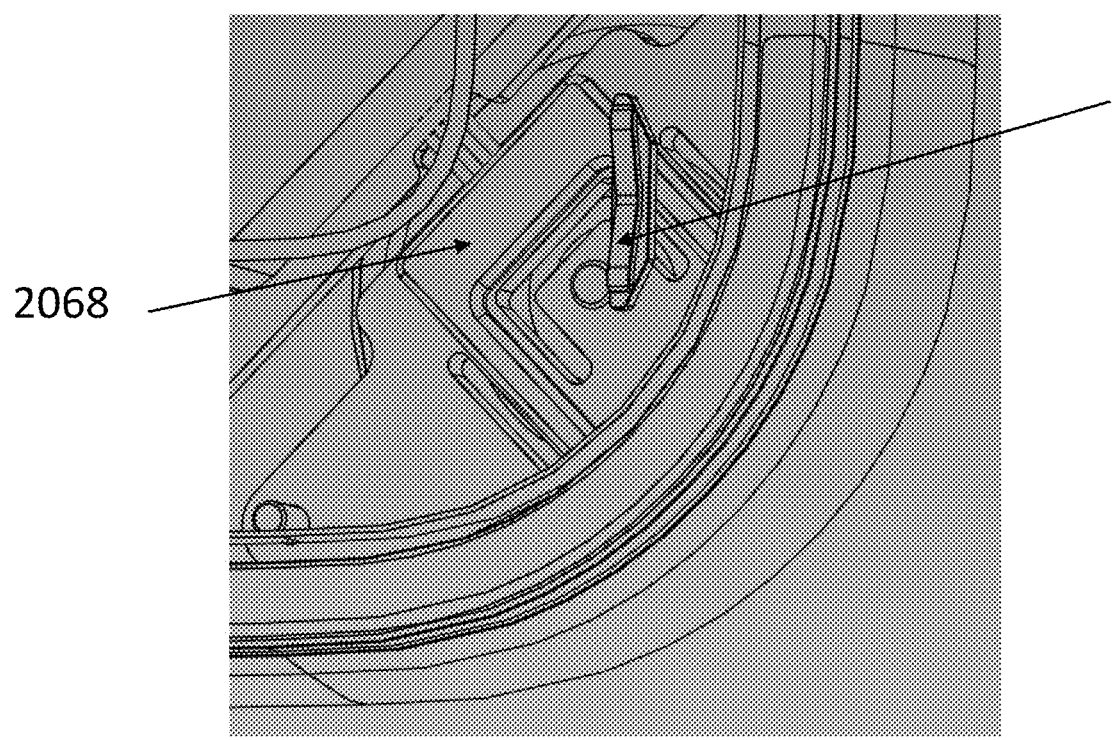
FIG. 32E illustrates an arrangement of a load cell and spacer in an imaging system.

FIGS. 32A-E schematically illustrate load cells useful in the system herein. FIG. 32A shows a top perspective view of load cell 2068 in a corner of platform 2000. To be used as a weight scale, as well as a foot imager, system 2020 is equipped with force sensors to measure patient weight. Typical commercially available load cells have form factors which are rectangular or square. However, in order to fit the square/rectangular load cell in the platform, the superimposition of a square/rectangular load cell over the area of the device where the scan head is moving around meant the load cell and the scanning volume were vertically stacked atop each other which rendered the platform thicker and larger. Disclosed herein are thin load cells with a generally triangular shape (as shown below). By locating the generally triangular load cell 2068 in a corner of platform 2000, load cell and the scanning volume do not need to be vertically stacked atop each other. Use of full-bridge load cells, as disclosed herein, improves the device's weight measurement performance on uneven surfaces, as are commonly found in homes. FIG. 32B shows load cell 2068. Load cell can be described as having a generally triangular shaped structure with a center portion 2070 and a first wing shape 2076a on a first side 2070 of center portion 2070 and a second wing shape 2076b on a second side of center portion 2070. Load cell 2068 includes a width w (at a widest part) and a length l (at a longest part) and the width w can bigger or about the same size as the length (e.g., 2× as big, 1.9× as big, 1.5×, etc.). Center portion 2070 includes a rounded apex 2082. FIG. 32B shows first wing shape 2076a of load cell 2068 includes leading edge 2078a and trailing edge 2076 and second wing shape 2076b includes leading edge 2078b and trailing edge 2076b. FIG. 32B shows an outside perimeter of load cell 2068 can include one or more inflection points, 2080a, 2080b, 2080c, 2080d. FIG. 32C and FIG. 32D show additional examples of load cells with respective center portions (2090, 2080) and respective first (2096a, 2086a) and second wings (2096b, 2086b). FIG. 32D illustrates a corner of a platform (such as platform 2000) with load cell 2068 and spacer 2010.

It should be understood that any feature described herein with respect to one embodiment can be used in addition to or in place of any feature described with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for detecting a foot abnormality, comprising:
   a platform, comprising a top layer with a first side and a second side, wherein the top layer comprises an optically clear tempered glass material, wherein the first side of the top layer is configured for engagement with a foot of a user;
   an imaging device within the platform, wherein the imaging device comprises a contact image sensor configured to image the foot of the user through the optically clear top layer while the foot is engaged with the top side of the platform, wherein the contact image sensor is configured to move relative to the top side of the platform to image the foot of the user;
   a pair of flexible spacers, each positioned against the second side of the top layer and at opposite ends of the contact image sensor, wherein the flexible spacers are configured to glide along the second side of the top layer, further wherein the flexible spacers are configured to deflect in response to a load on the top layer;
   a motor within the platform, wherein the motor is configured to drive the contact image sensor to move relative to the top side of the platform;
   a chassis within the platform and under the imaging device, wherein the chassis supports the imaging device, further wherein the chassis comprises a radiofrequency transparent material; and
   a linear rail in the platform, wherein the linear rail is between the imaging device and the chassis.

2. The system of claim 1, further comprising a processor.

3. The system of claim 2, wherein the processor is in the platform.

4. The system of claim 2, wherein the processor is configured to issue an alert flag indicating suspicion of a foot abnormality based on the plurality of images gathered by the imaging device.

5. The system of claim 1, wherein a base of the platform is less than 4 cm in height.

6. The system of claim 1, wherein the platform further comprises a scale configured to weigh the user.

7. The system of claim 1, further comprising a plurality of load cells, wherein the load cells are positioned horizontally to the imaging device, relative to a plane of the top layer of the platform.

8. The system of claim 1, wherein the imaging device is configured to produce images of the foot within less than 4 seconds of the time the sensor detects that the user has stepped on the platform.

9. A system for detecting a foot abnormality, comprising:
   a platform, comprising a top layer with a first side and a second side, wherein the top layer comprises an optically clear tempered glass material, wherein the first side of the top layer is configured for engagement with a foot of a user;
   an imaging device within the platform, wherein the imaging device comprises a contact image sensor configured to image the foot of the user through the optically clear top layer while the foot is engaged with the top side of the platform, wherein the contact image sensor is configured to move relative to the top side of the platform to image the foot of the user;
   a pair of flexible spacers, each positioned against the second side of the top layer and at opposite ends of the contact image sensor, wherein the flexible spacers are configured to glide along the second side of the top layer, further wherein the flexible spacers are configured to deflect in response to a load on the top layer;
   a motor within the platform, wherein the motor is configured to drive the contact image sensor to move relative to the top side of the platform;
   an encoder connected to the motor and configured to provide an output indicative of a contact image sensor position, wherein a controller is configured to use the output to direct the imaging device to obtain images when the contact image sensor is accelerating or decelerating;
   a chassis within the platform and under the imaging device, wherein the chassis supports the imaging device, further wherein the chassis comprises a radiofrequency transparent material; and
   a linear rail in the platform, wherein the linear rail is between the imaging device and the chassis.

10. The system of claim 9, further comprising a processor.

11. The system of claim 10, wherein the processor is in the platform.

12. The system of claim 10, wherein the processor is configured to issue an alert flag indicating suspicion of a foot abnormality based on the plurality of images gathered by the imaging device.

13. The system of claim 9, wherein a base of the platform is less than 4 cm in height.

14. The system of claim 9, wherein the platform further comprises a scale configured to weigh the user.

15. The system of claim 9, further comprising a plurality of load cells, wherein the load cells are positioned horizontal to the imaging device, relative to a plane of the top layer of the platform.

16. The system of claim 9, wherein the imaging device is configured to produce images of the foot within less than 4 seconds of the time the sensor detects that the user has stepped on the platform.

17. A system for detecting a foot abnormality, comprising:
- a platform, comprising a top layer with a first side and a second side, wherein the top layer comprises an optically clear tempered glass material, wherein the first side of the top layer is configured for engagement with a foot of a user;
- an imaging device within the platform, wherein the imaging device comprises a contact image sensor configured to image the foot of the user through the optically clear top layer while the foot is engaged with the top side of the platform, wherein the contact image sensor is configured to move relative to the top side of the platform to image the foot of the user;
- a pair of flexible spacers, each positioned against the second side of the top layer and at opposite ends of the contact image sensor, wherein the flexible spacers are configured to glide along the second side of the top layer, further wherein the flexible spacers are configured to deflect in response to a load on the top layer;
- a motor within the platform, wherein the motor is configured to drive the contact image sensor to move relative to the top side of the platform;
- an encoder connected to the motor and configured to provide an output indicative of a contact image sensor position, wherein a controller is configured to use the output to direct the imaging device to obtain images when the contact image sensor is accelerating or decelerating; and
- a chassis within the platform and under the imaging device, wherein the chassis supports the imaging device, further wherein the chassis comprises a radiofrequency transparent material.

18. A method of imaging a foot, comprising:
automatically detecting that a foot of a user has engaged with an imaging platform;
deflecting, with a load from the foot of the user, a top layer of the imaging platform;
flexing a pair of flexible spacers, wherein each flexible spacer is positioned against the second side of the top layer and at opposite ends of an imaging device, wherein the flexible spacers are configured to glide along the second side of the top layer during device imaging;
driving, with a motor, an imaging device in the imaging platform to move relative to the foot of the user, wherein the imaging device comprises a contact image sensor;
obtaining, with an encoder connected to the motor, an output indicative of a contact image sensor position, when the imaging device is accelerating or decelerating;
directing, with a controller, the imaging device to produce a plurality of images when the imaging device is accelerating or decelerating; and
processing the plurality of images to obtain a foot image.

19. The method of claim 18, further comprising detecting a foot abnormality based upon the plurality of images.

20. The method of claim 18, further comprising automatically determining if a foot abnormality is present based upon the plurality of images.

* * * * *